US007803916B2

(12) United States Patent  (10) Patent No.: US 7,803,916 B2
Afar et al.  (45) Date of Patent: Sep. 28, 2010

(54) GENE EXPRESSED IN PROSTATE CANCER

(75) Inventors: Daniel E. Afar, Fremont, CA (US);
Rene S. Hubert, Los Angeles, CA (US);
Stephen Chappell Mitchell, Gurnee, IL (US)

(73) Assignee: Agensys Inc., Santa Monica, CA (US)

( * ) Notice: Subject to any disclaimer, the term of this patent is extended or adjusted under 35 U.S.C. 154(b) by 38 days.

(21) Appl. No.: 12/211,702

(22) Filed: Sep. 16, 2008

(65) Prior Publication Data
US 2009/0098629 A1 Apr. 16, 2009

Related U.S. Application Data

(62) Division of application No. 10/334,561, filed on Dec. 30, 2002, now Pat. No. 7,432,346, which is a division of application No. 09/410,132, filed on Sep. 30, 1999, now Pat. No. 6,509,458.

(60) Provisional application No. 60/146,584, filed on Jul. 28, 1999, provisional application No. 60/102,572, filed on Sep. 30, 1998.

(51) Int. Cl.
*C07K 16/00* (2006.01)
*C12N 5/12* (2006.01)
(52) U.S. Cl. ............ 530/387.1; 530/397.1; 530/397.3; 435/326
(58) Field of Classification Search .................. None
See application file for complete search history.

(56) References Cited

U.S. PATENT DOCUMENTS

| 5,912,143 | A | 6/1999 | Bandman et al. |
| 6,166,194 | A | 12/2000 | Wong et al. |
| 2007/0298491 | A1* | 12/2007 | Rosen et al. ................ 435/325 |

FOREIGN PATENT DOCUMENTS

| WO | WO-96/18730 | 6/1996 |
| WO | WO-98/40403 | 9/1998 |
| WO | WO9859071 | * 12/1998 |
| WO | WO-00/18925 | 6/2000 |
| WO | WO-00/61779 | 10/2000 |
| WO | WO-01/53836 | 7/2001 |

OTHER PUBLICATIONS

EMBL Database, Accession No. AA145922 (1996).
EMBL Database, Accession No. BX161415 (2003).
Israeli Office Action for Application No. 142194, date mailed on Jul. 16, 2007, 2 pages (Translation Only).
Reiger et al., Glossary of Genetics and Cytogenetics, Classical and Molecular, 4th ed., Springer-Verlay, Berlin, (1976).
Alberts et al., Molecular Biology of the Cell, 3rd ed., (1994) p. 465.
Ellis et al., U.S. Patent No. 5,922,546, Aug. 25, 1997, Issued U.S. Patent Sequences Database, Results 1.
Shantz and Pegg, Int. J. of Biochem. And Cell Biol. (1999) 31:107-122.
McClean and Hill, Eur. J. of Cancer (1993) 29A:2243-2248.
Fu et al., EMBO Journal (1996) 15:4392-4401.
Marra et al., "The WashU-HHMI Mouse EST Project," EMBL Database Acc. No. AA145922, Dec. 14, 1996, XP002132118, Abstract.
Strausberg et al., "National Cancer Institute, Cancer Genome Anatomy Project (OGAP)," 1999, EMBL Database Acc. No. AI808141, Jul. 8, 1999, XP 002132119, Abstract.
Strausberg, Aug. 30, 1999, dbEST Id 2960907, GenBank Acc. AI872360.
International Search Report from PCT Application No. PCT/US99/23005, 1999.
U.S. Appl. No. 09/410,132, filed by Afar et al., Sep. 30, 1999.
Preliminary Amendment from U.S. Appl. No. 09/410,132, filed Jan. 26, 2000.
Non-Final Office Action from U.S. Appl. No. 09/410,132, mailed on Nov. 21, 2000.
Amendment Under 37 C.F.R. § 1.111 from U.S. Appl. No. 09/410,132, filed Apr. 23, 2001.
Final Office Action from U.S. Appl. No. 09/410,132, mailed on Jul. 17, 2001.
Amendment Under 37 C.F.R. § 1.116 from U.S. Appl. No. 09/410,132, filed Nov. 19, 2001.
Advisory Action from U.S. Appl. No. 09/410,132, mailed on Jan. 29, 2002.
Declaration of Pia M. Challita-Eid from U.S. Appl. No. 09/410,132, filed Jul. 17, 2002.
Notice of Allowance from U.S. Appl. No. 09/410,132, mailed on Aug. 27, 2002.
Examiner's First Report on Australian Patent Application No. 62855/99, dated Jun. 21, 2002.
Request to Amend a Complete Specification for Australian Patent Application No. 62855/99, dated Jun. 18, 2003.
Office Action from Canadian Patent Application No. 2,344,620, dated Jul. 31, 2007.
Office Action from EP Patent Application No. 99 950 130.7-2405, dated Jun. 8, 2005.
Response to Office Action from EP Patent Application No. 99 950 130.7-2405, dated Oct. 13, 2005.

(Continued)

*Primary Examiner*—Larry R. Helms
*Assistant Examiner*—Lei Yao
(74) *Attorney, Agent, or Firm*—Morrison & Foerster LLP

(57) ABSTRACT

A novel testis-specific gene expressed in human prostate cancer, designated 22P4F11, is described. Analysis of 22P4F11 mRNA expression in normal prostate, prostate tumor xenografts, and a variety of normal tissues indicates that the expression of this gene is testis specific in normal tissues. The 22P4F11 gene is also expressed in human prostate tumors, in some cases at high levels. A full length cDNA encoding 22P4F11 is provided. The 22P4F11 transcript and/or protein may represent a useful diagnostic marker and/or therapeutic target for prostate cancer.

16 Claims, 6 Drawing Sheets

OTHER PUBLICATIONS

Office Action from EP Patent Application No. 99 950 130.7-2405, dated Jan. 8, 2007.
Response to Office Action from EP Patent Application No. 99 950 130.7-2405, dated May 18, 2007.
Office Action from EP Patent Application No. 99 950 130.7-2405, dated Jun. 8, 2007.
Notification of Defects in Israeli Patent Application No. 142194, dated Apr. 15, 2007.
Submissions for Israeli Patent Application No. 142194, dated Jul. 9, 2007.
Notification of Defects in Israeli Patent Application No. 142194, dated Jul. 16, 2007.
Examiner's First Report on Australian Patent Application No. 2003259622, dated Jul. 14, 2005.
Request to Amend a Complete Specification for Australian Patent Application No. 2003259622, dated Sep. 21, 2005.
Examiner's Report No. 2 on Australian Patent Application No. 2003259622, dated Oct. 7, 2005.
Request to Amend a Complete Specification for Australian Patent Application No. 2003259622, dated Jun. 7, 2006.
Bellone et al., Immunology Today (1999) 20(10):457-462.
Gaiger et al., Blood (2000) 96(4):1480-1489.
Greenbaum et al., Genome Biology (2003) 4(9):117.1-117.8.
Lewin (ed.), Genes VI, Oxford University Press (1997) Ch. 29, pp. 847-848.
Slamon et al., Science (1987) 235:177-182.
Tockman et al., Cancer Res. (1992) 52:2711s-2718s.

* cited by examiner

FIGURE 1A-1

```
             11          20          29          38          47          56
5' AAA ACA GGC TGG TAC CGG TCC GGA ATT CCC GGG ATA TCG TCG ACC CAC GCG TCC
   --- --- --- --- --- --- --- --- --- --- --- --- --- --- --- --- --- ---
             65          74          83          92         101         110
   GGA GAA ACT ATA ATG ATA ATT TCT ACC AGG AGA TTT TCT TAA TTA ACT CTG TGA
   --- --- --- --- --- --- --- --- --- --- --- --- --- --- --- --- --- ---
            119         128         137         146         155         164
   AAG ATT AGC TTC AAT GTC TTA ATT TCA CAG ATG ATA CAA AGA ATG GTT AAA TGA
   --- --- --- --- --- --- --- --- --- --- --- --- --- --- --- --- --- ---
            173         182         191         200         209         218
   GTG TTT CAA AAA CTC TGA TAG AAA CAA GAA TTT ATT TTA TGA TTA AAT TTC AGT
   --- --- --- --- --- --- --- --- --- --- --- --- --- --- --- --- --- ---
            227         236         245         254         263         272
   CCA TTA TGA TTT TCC TTT CTC ACA TAA TTA CTT TTT TCT TTT TAG ACT TAT AAG
   --- --- --- --- --- --- --- --- --- --- --- --- --- --- --- --- --- ---
    P   L   *   F   S   F   L   T   *   L   L   F   S   F   *   T   Y   K 281         290         299         308         317         326
   CTA GCA ATT ACA GAT TTA ACT ACA GCT ATC AGC ATG GAC AAA AAT AGT TAT ACA
   --- --- --- --- --- --- --- --- --- --- --- --- --- --- --- --- --- ---
    L   A   I   T   D   L   T   T   A   I   S   M   D   K   N   S   Y   T 335         344         353         362         371         380
   GCA TTT TAT AAC AGA GCA TTA TGT TAC ACC AAG ATA AGG GAA CTT CAA ATG GCA
   --- --- --- --- --- --- --- --- --- --- --- --- --- --- --- --- --- ---
    A   F   Y  [N   R   A   L   C   Y]  T   K   I   R   E   L   Q   M   A 389         398         407         416         425         434
   TTA ACA GAT TAT GGA ATT GTG CTG CTT CTT GAT GCT ACA GAA ACT GTA AAA CTA
   --- --- --- --- --- --- --- --- --- --- --- --- --- --- --- --- --- ---
    L   T   D   Y   G   I   V   L   L   L   D   A   T   E   T   V   K   L 443         452         461         470         479         488
   AAT ACC TTC CTT AAT CGT GGA CTC ATC TAC GTA GAA CTA GGC CAG TAT GGC TTT
   --- --- --- --- --- --- --- --- --- --- --- --- --- --- --- --- --- ---
    N   T   F   L   N   R   G   L   I   Y   V   E   L   G   Q   Y   G   F 497         506         515         524         533         542
   GCA CTA GAG GAT TTT AAA CAA GCT GCA CTG ATA AGC CGG ACT AAC GGG AGC CTT
   --- --- --- --- --- --- --- --- --- --- --- --- --- --- --- --- --- ---
    A   L   E   D   F   K   Q   A   A   L   I   S   R   T   N   G   S   L 551         560         569         578         587         596
   TGT CAC GCC ACT GCC ATG TGC CAT CAC AGA ATT AAT GAG TTT GAA GAA GCT GTC
   --- --- --- --- --- --- --- --- --- --- --- --- --- --- --- --- --- ---
    C   H   A   T   A   M   C   H   H   R   I   N   E   F   E   E   A   V 605         614         623         632         641         650
   AAT TTC TTT ACT TGG GCT CTT AAA ATT AAC CCA TGT TTT CTG GAT GCT TAT GTT
   --- --- --- --- --- --- --- --- --- --- --- --- --- --- --- --- --- ---
    N   F   F   T   W   A   L   K   I   N   P   C   F   L   D   A   Y   V 659         668         677         686         695         704
   GGA CGG GGA AAT TCT TAC ATG GAA TAC GGT CAT GAT GAA GCC ACC AAG CAA GCA
   --- --- --- --- --- --- --- --- --- --- --- --- --- --- --- --- --- ---
    G   R   G   N   S   Y   M   E   Y   G   H   D   E   A   T   K   Q   A
```

FIGURE 1A-2

```
        713             722             731             740             749             758
CAG AAA GAC TTT CTG AAA GCA CTG CAT ATT AAT CCA GCA TAC ATA AAA GCC AGA
--- --- --- --- --- --- --- --- --- --- --- --- --- --- --- --- --- ---
 Q   K   D   F   L   K   A   L   H   I   N   P   A   Y   I   K   A   R 767             776             785             794             803             812
ATT AGT TTT GGC TAT AAT TTG CAG GCC CAA GGA AAA TTC CAG AAA GCT TGG AAC
--- --- --- --- --- --- --- --- --- --- --- --- --- --- --- --- --- ---
 I   S   F   G   Y   N   L   Q   A   Q   G   K   F   Q   K   A   W   N 821             830             839             848             857             866
CAC TTT ACC ATT GCC ATA GAT ACT GAT CCA AAG AAC TAC CTA GCC TAT GAA GGA
--- --- --- --- --- --- --- --- --- --- --- --- --- --- --- --- --- ---
 H   F   T   I   A   I   D   T   D   P   K   N   Y   L   A   Y   E   G 875             884             893             902             911             920
AGA GCT GTG GTC TGT CTT CAG ATG GGT AAT AAT TTT GCT GCA ATG CAG GAT ATT
--- --- --- --- --- --- --- --- --- --- --- --- --- --- --- --- --- ---
 R   A   V   V   C   L   Q   M   G   N   N   F   A   A   M   Q   D   I 929             938             947             956             965             974
AAT GCT GCC ATG AAG ATC AGT ACT ACA GCA GAA TTC TTA ACA AAT CGT GGG GTG
--- --- --- --- --- --- --- --- --- --- --- --- --- --- --- --- --- ---
 N   A   A   M   K   I   S   T   T   A   E   F   L   T   N   R   G   V 983             992            1001            1010            1019            1028
ATT CAT GAG TTT ATG GGC CAC AAA CAG AAT GCA ATG AAA GAC TAC CAA GAT GCA
--- --- --- --- --- --- --- --- --- --- --- --- --- --- --- --- --- ---
 I   H   E   F   M   G   H   K   Q   N   A   M   K   D   Y   Q   D   A 1037            1046            1055            1064            1073            1082
ATT ACT CTA AAC CCC AAG TAC TCG CTG GCT TAC TTT AAT GCA GGA AAT ATC TAC
--- --- --- --- --- --- --- --- --- --- --- --- --- --- --- --- --- ---
 I   T   L   N   P   K   Y   S   L   A   Y   F   N   A   G   N   I   Y 1091            1100            1109            1118            1127            1136
TTT CAC CAC AGG CAG TTT TCC CAG GCC AGT GAC TAC TTC TCA AAA GCT TTA AAA
--- --- --- --- --- --- --- --- --- --- --- --- --- --- --- --- --- ---
 F   H   H   R   Q   F   S   Q   A   S   D   Y   F   S   K   A   L   K 1145            1154            1163            1172            1181            1190
TTT GAT CCA GAA AAT GAA TAT GTT CTC ATG AAT CGA GCT ATT ACA AAT ACA ATA
--- --- --- --- --- --- --- --- --- --- --- --- --- --- --- --- --- ---
 F   D   P   E   N   E   Y   V   L   M   N   R   A   I   T   N   T   I 1199            1208            1217            1226            1235            1244
TTA AAG AAA TAT GAA GAA GCA AAA GAA GAT TTT GCA AAT GTA ATT GAA AGC TGT
--- --- --- --- --- --- --- --- --- --- --- --- --- --- --- --- --- ---
 L   K   K   Y   E   E   A   K   E   D   F   A   N   V   I   E   S   C 1253            1262            1271            1280            1289            1298
CCC TTT TGG GCT GCA GTA TAT TTT AAT AGA GCA CAT TTC TAC TAC TGC TTA AAG
--- --- --- --- --- --- --- --- --- --- --- --- --- --- --- --- --- ---
 P   F   W   A   A   V   Y   F   N   R   A   H   F   Y   Y   C   L   K 1307            1316            1325            1334            1343            1352
CAA TAT GAA CTA GCT GAG GAA GAC CTT AAT AAA GCC CTG TCT TTG AAG CCT AAT
--- --- --- --- --- --- --- --- --- --- --- --- --- --- --- --- --- ---
 Q   Y   E   L   A   E   E   D   L   N   K   A   L   S   L   K   P   N
```

FIGURE 1A-3

```
        1361        1370        1379        1388        1397        1406
GAT GCT CTA GTA TAT AAT TTT AGA GCA AAA GTT CGT GGT AAA ATA GGT CTG ATT
--- --- --- --- --- --- --- --- --- --- --- --- --- --- --- --- --- ---
 D   A   L   V   Y   N   F   R   A   K   V   R   G   K   I   G   L   I 1415        1424        1433        1442        1451        1460
GAG GAA GCT ATG GCT GAC TAT AAC CAA GCA CTT GAT CTT GAA GAC TAT GCC TCA
--- --- --- --- --- --- --- --- --- --- --- --- --- --- --- --- --- ---
 E   E   A   M   A   D   Y   N   Q   A   L   D   L   E   D   Y   A   S 1469        1478        1487        1496        1505        1514
GTT ATA TGA TTA CAT AGA CTG TGG TTG CTA TAG TAG TTT ACA CAG CTG TTC TCT
--- --- --- --- --- --- --- --- --- --- --- --- --- --- --- --- --- ---
 V   I   *

1523        1532        1541        1550        1559        1568
CTG AAA CGG AAA CAT ATT TGT TGT CTA AAA GGT TCT ACC ATT TTC ATT ATT GTA
--- --- --- --- --- --- --- --- --- --- --- --- --- --- --- --- --- ---
        1577        1586        1595        1604        1613        1622
TTC GTT ATG CTT AGT CTT CCA TAT AAC CTT CTA TGC ATT TTA ATA AAA TGT TTG
--- --- --- --- --- --- --- --- --- --- --- --- --- --- --- --- --- ---
        1631        1640        1649        1658        1667        1676
TTA TAC ATT AAT TAT AAA ACA TAT ATC ATT TGC TGC ATA TTT GGA ATA CCT TGA
--- --- --- --- --- --- --- --- --- --- --- --- --- --- --- --- --- ---
        1685        1694        1703        1712        1721        1730
GAA CTG AAT TTT TCC AAG GTT GCA GAA TCT CAA GGA AAA TGT TTC TTA AGG AAT
--- --- --- --- --- --- --- --- --- --- --- --- --- --- --- --- --- ---
        1739        1748        1757        1766        1775        1784
TAA ATA GGA ATG TCT CTT AAC ATT TAA AAT ATT TTC TTT AAT TCT TTT TGA AAT
--- --- --- --- --- --- --- --- --- --- --- --- --- --- --- --- --- ---
        1793        1802        1811        1820        1829        1838
AAT ACT ATA CAT TGT AGA AAA AGT GTC ATT GAC CTT TTC ATC AGT CCT TGC TGA
--- --- --- --- --- --- --- --- --- --- --- --- --- --- --- --- --- ---
        1847        1856        1865        1874        1883        1892
CAA TGT ATT AAA CAG TAT ACA GAT TAA AAA TAA ACA AAC CGA TGA CTA TAA AAA
--- --- --- --- --- --- --- --- --- --- --- --- --- --- --- --- --- ---
        1901        1910        1919        1928        1937        1946
ACT GAA CTC AAG TAC AAC CCT TCT CTT TTC CTT TAA ACA ATA TGT ATA CTG GTC
--- --- --- --- --- --- --- --- --- --- --- --- --- --- --- --- --- ---
        1955        1964        1973        1982        1991        2000
AAT ATT CTT CCT GAT ACC TAT ATT CTT CCA ACA GAC AAA CGT GTT TCT CTT TTA
--- --- --- --- --- --- --- --- --- --- --- --- --- --- --- --- --- ---
        2009        2018        2027        2036        2045        2054
CAT GTG GCC TGC CTT CTA GGA CAG TAC CTA TAA AGA TTT TGG ACA TCA TGT TTC
--- --- --- --- --- --- --- --- --- --- --- --- --- --- --- --- --- ---
        2063        2072        2081        2090        2099        2108
CTT GAG ATA GTT CCC TCT GCC TCT TTA ATG CAG CTA TCA TAA ATA CAT GTA AAA
--- --- --- --- --- --- --- --- --- --- --- --- --- --- --- --- --- ---
        2117        2126        2135        2144        2153        2162
TTT GTA TAT ATT TAT AAT TCA TGC ATT GCA GGA GTT GAT GAG TGA AAA TAA AAC
--- --- --- --- --- --- --- --- --- --- --- --- --- --- --- --- --- ---
        2171        2180        2189        2198        2207        2216
AAC TAA AAA TTA AAA AAA AAA AAA AAA AAG GGC GGC CGC TCT AGA GTA TCC CTC
--- --- --- --- --- --- --- --- --- --- --- --- --- --- --- --- --- ---
        2225        2234        2243
GAG GGG CCC AAG CTT ACG CGT ACC CAG CTT TCT TG 3'
--- --- --- --- --- --- --- --- --- --- --- --
```

FIGURE 1B

```
            10           19           28           37           46           55
5' ATC AGT ACT ACA GCA GAA TTC TTA ACA AAT CGT GGG GTG ATT CAT GAG TTT ATG
   --- --- --- --- --- --- --- --- --- --- --- --- --- --- --- --- --- ---
   Ile Ser Thr Thr Ala Glu Phe Leu Thr Asn Arg Gly Val Ile His Glu Phe Met 64           73           82           91          100          109
   GGC CAC AAA CAG AAT GCA ATG AAA GAC TAC CAA GAT GCA ATT ACT CTA AAC CCC
   --- --- --- --- --- --- --- --- --- --- --- --- --- --- --- --- --- ---
   Gly His Lys Gln Asn Ala Met Lys Asp Tyr Gln Asp Ala Ile Thr Leu Asn Pro 118          127          136          145          154          163
   AAG TAC TCG CTG GCT TAC TTT AAT GCA GGA AAT ATC TAC TTT CAC CAC AGG CAG
   --- --- --- --- --- --- --- --- --- --- --- --- --- --- --- --- --- ---
   Lys Tyr Ser Leu Ala Tyr Phe Asn Ala Gly Asn Ile Tyr Phe His His Arg Gln 172          181          190          199          208
   TTT TCC CAG GCC AGT GAC TAC TTC TCA AAA GCT TTA AAA TTT GAT 3'
   --- --- --- --- --- --- --- --- --- --- --- --- --- --- ---
   Phe Ser Gln Ala Ser Asp Tyr Phe Ser Lys Ala Leu Lys Phe Asp
```

FIGURE 2
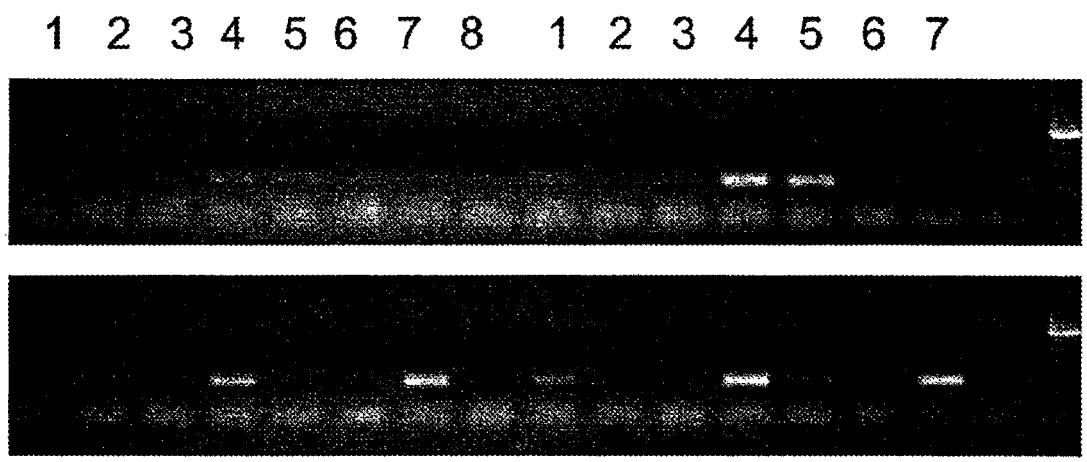
Panels:
A
1. Brain
2. Prostate
3. LAPC-4 AD
4. LAPC-4 AI
5. LAPC-9 AD
6. HeLa
7. Murine cDNA
8. Neg. control
B
1. Brain
2. Heart
3. Kidney
4. Liver
5. Lung
6. Pancreas
7. Placenta
8. Skeletal Muscle
C
1. Colon
2. Ovary
3. Leukocytes
4. Prostate
5. Small Intestine
6. Spleen
7. Testis
8. Thymus

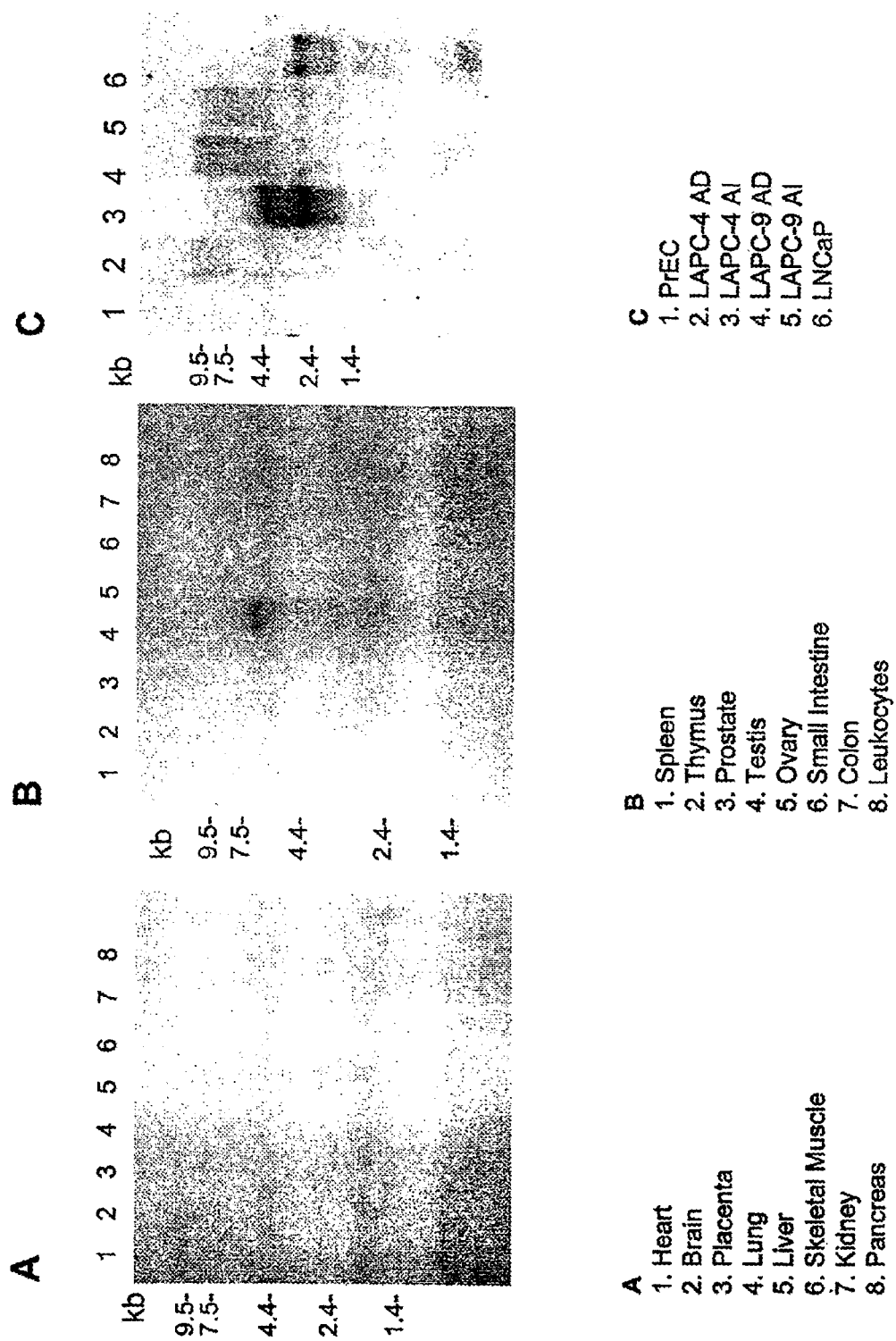

GENE EXPRESSED IN PROSTATE CANCER

CROSS-REFERENCE TO RELATED APPLICATIONS

This application is a divisional of U.S. application Ser. No. 10/334,561 filed 30 Dec. 2002, now U.S. Pat. No. 7,432,346, which is a divisional of U.S. application Ser. No. 09/410,132 filed 30 Sep. 1999 which issued as U.S. Pat. No. 6,509,458 which claims benefit under 35 USC §119(e) to U.S. Ser. No. 60/146,584 filed 28 Jul. 1999 and of U.S. Ser. No. 60/102,572 filed 30 Sep. 1998. The contents of these documents are incorporated herein by reference.

Throughout this application, various publications are referenced within parentheses. The disclosures of these publications are hereby incorporated by reference herein in their entireties.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

FIELD OF THE INVENTION

The invention described herein relates to a novel gene and its encoded proteins, termed 22P4F11, and to diagnostic and therapeutic methods and compositions useful in the management of various cancers which express 22P4F11, particularly including prostate cancers.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 511582003111Seqlist.txt | Sep. 12, 2008 | 9,864 bytes |

BACKGROUND OF THE INVENTION

Cancer is the second leading cause of human death next to coronary disease. Worldwide, millions of people die from cancer every year. In the United States alone, cancer causes the death of well over a half-million people annually, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Many cancer patients experience a recurrence.

Generally speaking, the fundamental problem in the management of the deadliest cancers is the lack of effective and non-toxic systemic therapies. Molecular medicine promises to redefine the ways in which these cancers are managed. Unquestionably, there is an intensive worldwide effort aimed at the development of novel molecular approaches to cancer diagnosis and treatment. For example, there is a great interest in identifying truly tumor-specific genes and proteins that could be used as diagnostic and prognostic markers and/or therapeutic targets or agents. Research efforts in these areas are encouraging, and the increasing availability of useful molecular technologies has accelerated the acquisition of meaningful knowledge about cancer. Nevertheless, progress is slow and generally uneven.

As discussed below, the management of prostate cancer serves as a good example of the limited extent to which molecular biology has translated into real progress in the clinic. With limited exceptions, the situation is more or less the same for the other major carcinomas mentioned above.

Worldwide, prostate cancer is the fourth most prevalent cancer in men. In North America and Northern Europe, it is by far the most common male cancer and is the second leading cause of cancer death in men. In the United States alone, well over 40,000 men die annually of this disease—second only to lung cancer. Despite the magnitude of these figures, there is still no effective treatment for metastatic prostate cancer. Surgical prostatectomy, radiation therapy, hormone ablation therapy, and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the management of this disease. Although the serum PSA assay has been a very useful tool, its specificity and general utility is widely regarded as lacking in several important respects.

Most prostate cancers initially occur in the peripheral zone of the prostate gland, away from the urethra. Tumors within this zone may not produce any symptoms and, as a result, most men with early-stage prostate cancer will not present clinical symptoms of the disease until significant progression has occurred. Tumor progression into the transition zone of the prostate may lead to urethral obstruction, thus producing the first symptoms of the disease. However, these clinical symptoms are indistinguishable from the common non-malignant condition of benign prostatic hyperplasia (BPH). Early detection and diagnosis of prostate cancer currently relies on digital rectal examinations (DRE), prostate specific antigen (PSA) measurements, transrectal ultrasonography (TRUS), and transrectal needle biopsy (TRNB). At present, serum PSA measurement in combination with DRE represent the leading tool used to detect and diagnose prostate cancer. Both have major limitations which have fueled intensive research into finding better diagnostic markers of this disease.

Similarly, there is no available marker that can predict the emergence of the typically fatal metastatic stage of prostate cancer. Diagnosis of metastatic stage is presently achieved by open surgical or laparoscopic pelvic lymphadenectomy, whole body radionuclide scans, skeletal radiography, and/or bone lesion biopsy analysis. Clearly, better imaging and other less invasive diagnostic methods offer the promise of easing the difficulty those procedures place on a patient, as well as improving diagnostic accuracy and opening therapeutic options. A similar problem is the lack of an effective prognostic marker for determining which cancers are indolent and which ones are or will be aggressive. PSA, for example, fails to discriminate accurately between indolent and aggressive cancers. Until there are prostate tumor markers capable of reliably identifying early-stage disease, predicting susceptibility to metastasis, and precisely imaging tumors, the management of prostate cancer will continue to be extremely difficult.

PSA is the most widely used tumor marker for screening, diagnosis, and monitoring prostate cancer today. In particular, several immunoassays for the detection of serum PSA are in widespread clinical use. Recently, a reverse transcriptase-polymerase chain reaction (RT-PCR) assay for PSA mRNA in serum has been developed. However, PSA is not a disease-specific marker, as elevated levels of PSA are detectable in a large percentage of patients with BPH and prostatitis (25-86%) (Gao et al., 1997, Prostate 31: 264-281), as well as in other nonmalignant disorders and in some normal men, a factor which significantly limits the diagnostic specificity of this marker. For example, elevations in serum PSA of between 4 to 10 ng/ml are observed in BPH, and even higher values are observed in prostatitis, particularly acute prostatitis. BPH is an extremely common condition in men. Further confusing the situation is the fact that serum PSA elevations may be observed without any indication of disease from DRE, and visa-versa. Moreover, it is now recognized that PSA is not prostate-specific (Gao et al., supra, for review).

Various methods designed to improve the specificity of PSA-based detection have been described, such as measuring PSA density and the ratio of free vs. complexed PSA. However, none of these methodologies have been able to reproducibly distinguish benign from malignant prostate disease. In addition, PSA diagnostics have sensitivities of between 57-79% (Cupp & Osterling, 1993, Mayo Clin Proc 68:297-306), and thus miss identifying prostate cancer in a significant population of men with the disease.

There are some known markers which are expressed predominantly in prostate, such as prostate specific membrane antigen (PSM), a hydrolase with 85% identity to a rat neuropeptidase (Carter et al., 1996, Proc. Natl. Acad. Sci. USA 93: 749; Bzdega et al., 1997, J. Neurochem. 69: 2270). However, the expression of PSM in small intestine and brain (Israeli et al., 1994, Cancer Res. 54: 1807), as well its potential role in neuropeptide catabolism in brain, raises concern of potential neurotoxicity with anti-PSM therapies. Preliminary results using an Indium-111 labeled, anti-PSM monoclonal antibody to image recurrent prostate cancer show some promise (Sodee et al., 1996, Clin Nuc Med 21: 759-766). More recently identified prostate cancer markers include PCTA-1 (Su et al., 1996, Proc. Natl. Acad. Sci. USA 93: 7252) and prostate stem cell antigen (PSCA) (Reiter et al., 1998, Proc. Natl. Acad. Sci. USA 95: 1735). PCTA-1, a novel galectin, is largely secreted into the media of expressing cells and may hold promise as a diagnostic serum marker for prostate cancer (Su et al., 1996). PSCA, a GPI-linked cell surface molecule, was cloned from LAPC-4 cDNA and is unique in that it is expressed primarily in basal cells of normal prostate tissue and in cancer epithelia (Reiter et al., 1998). Vaccines for prostate cancer are also being actively explored with a variety of antigens, including PSM and PSA.

SUMMARY OF THE INVENTION

The present invention relates to a novel gene expressed in prostate cancer cells, designated 22P4F11. Analysis of 22P4F11 mRNA expression in normal prostate, prostate tumor xenografts, and a variety of normal tissues indicates that the expression of this gene is testis specific in normal tissues. The 22P4F11 gene is also expressed in human prostate cancer xenograft tumors, in some cases at high levels. A full length cDNA encoding 22P4F11 is provided. The 22P4F11 transcript and/or protein may represent a useful diagnostic marker and/or therapeutic target for prostate cancer.

The invention provides polynucleotides corresponding or complementary to all or part of the 22P4F11 genes, mRNAs, and/or coding sequences, preferably in isolated form, including polynucleotides encoding 22P4F11 proteins and fragments thereof, DNA, RNA, DNA/RNA hybrid, and related molecules, polynucleotides or oligonucleotides complementary to the 22P4F11 genes or mRNA sequences or parts thereof, and polynucleotides or oligonucleotides which hybridize to the 22P4F11 genes, mRNAs, or to 22P4F11-encoding polynucleotides. Also provided are means for isolating cDNAs and the genes encoding 22P4F11. Recombinant DNA molecules containing 22P4F11 polynucleotides, cells transformed or transduced with such molecules, and host-vector systems for the expression of 22P4F11 gene products are also provided. The invention further provides 22P4F11 proteins and polypeptide fragments thereof. The invention further provides antibodies that bind to 22P4F11 proteins and polypeptide fragments thereof, including polyclonal and monoclonal antibodies, murine and other mammalian antibodies, chimeric antibodies, humanized and fully human antibodies, antibodies labeled with a detectable marker. The invention further provides methods for detecting the presence of 22P4F11 polynucleotides and proteins in various biological samples, as well as methods for identifying cells that express 22P4F11. The invention further provides various therapeutic compositions and strategies for treating cancers which express 22P4F11 such as prostate cancers, including therapies aimed at inhibiting the transcription, translation, processing or function of 22P4F11 and cancer vaccines.

BRIEF DESCRIPTION OF THE FIGURES

FIG. 1A. Nucleotide and deduced amino acid sequences of a full length cDNA encoding the 22P4F11 gene (SEQ ID NOS: 1 and 2, respectively). The consensus Kozak sequence and start methionine are indicated in bold, and a putative mitochondrial signal sequence is boxed.

FIG. 1B. Nucleotide and ORF amino acid sequences of SSH-isolated 22P4F11 cDNA (SEQ ID NOS: 3 and 4, respectively).

FIG. 2. RT-PCR analysis of 22P4F11 gene expression in prostate cancer xenografts, normal prostate, and other tissues and cell lines, showing expression in prostate cancer xenografts and normal prostate at approximately equal levels (Panel A); and showing expression in normal tissues is highest in prostate, testis, lung and liver (Panels B and C).

FIG. 3. Northern blot analysis of 22P4F11 gene expression in a variety of normal human tissues and various prostate cancer xenografts, showing testis-specific expression in normal tissues and in some of the prostate cancer tissues. FIGS. 3A and 3B show the results of Northern blot analysis of samples taken from various normal human tissues using labeled 22P4F11-GTP3E10 cDNA as a probe. RNA samples were quantitatively normalized with a actin probe. Expression was only detected in testis. FIG. 3C shows analysis of RNAs derived from human prostate cancer xenografts, normal prostate and a prostate cancer cell line. Strong expression was detected in one of the LAPC-4 xenografts, and lower level expression was detected in the LNCaP prostate cancer cell line and in some of the other xenografts.

DETAILED DESCRIPTION OF THE INVENTION

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the terms "advanced prostate cancer", "locally advanced prostate cancer", "advanced disease" and "locally advanced disease" mean prostate cancers which have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

As used herein, the terms "metastatic prostate cancer" and "metastatic disease" mean prostate cancers which have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is the preferred treatment modality. Patients with metastatic prostate cancer eventually develop an androgen-refractory state within 12 to 18 months of treatment initiation, and approximately half of these patients die within 6 months thereafter. The most common site for prostate cancer metastasis is bone. Prostate cancer bone metastases are, on balance, characteristically osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA.

As used herein, the term "polypeptide" means a polymer of at least 10 amino acids. Throughout the specification, standard three letter or single letter designations for amino acids are used.

As used herein, the terms "hybridize", "hybridizing", "hybridizes" and the like, used in the context of polynucleotides, are meant to refer to conventional hybridization conditions, preferably such as hybridization in 50% formamide/6×SSC/0.1% SDS/100 µg/ml ssDNA, in which temperatures for hybridization are above 37 degrees C. and temperatures for washing in 0.1×SSC/0.1% SDS are above 55 degrees C., and most preferably to stringent hybridization conditions.

In the context of amino acid sequence comparisons, the term "identity" is used to express the percentage of amino acid residues at the same relative position which are the same. Also in this context, the term "homology" is used to express the percentage of amino acid residues at the same relative positions which are either identical or are similar, using the conserved amino acid criteria of BLAST analysis, as is generally understood in the art. Further details regarding amino acid substitutions, which are considered conservative under such criteria, are provided below.

Additional definitions are provided throughout the subsections which follow.

Structure and Expression of 22P4F11

As is further described in the Examples which follow, the 22P4F11 genes and proteins have been characterized using a number of analytical approaches. For example, analyses of nucleotide coding and amino acid sequences were conducted in order to identify potentially related molecules and three distinct 22P4F11 isoforms, as well as recognizable structural domains, topological features, and other elements within the 22P4F11 mRNA and protein structures. RT-PCR and Northern blot analyses of 22P4F11 mRNA expression were also conducted.

A full length cDNA encoding the 22P4F11 gene has been isolated. The nucleotide and deduced amino acid sequences of this cDNA are shown in FIG. 1A (SEQ ID NOS: 1 and 2, respectively). The nucleotide sequence of the initially isolated cDNA fragment corresponding to and identifying the 22P4F11 gene is provided in FIG. 1B (SEQ ID NOS: 3 and 4). This sequence shows no homology with any known genes or ESTs, and contains an open reading frame encoding 69 amino acids (FIG. 1B).

Expression analysis by RT-PCR shows that 22P4F11 is expressed in androgen-dependent and androgen-independent LAPC prostate cancer xenografts and in normal prostate at approximately equal levels (FIG. 2). In normal tissues, expression of the 22P4F11 gene appears somewhat restricted, with the highest levels of expression observed in prostate, testis, lung and liver tissues (FIG. 2). Northern blot analysis using a full length 22P4F11 cDNA probe, however, shows testis-specific expression in normal tissues as well as expression in prostate cancer xenografts, but no expression in normal prostate (FIG. 3).

22P4F11 Polynucleotides

One aspect of the invention provides polynucleotides corresponding or complementary to all or part of a 22P4F11 gene, mRNA, and/or coding sequence, preferably in isolated form, including polynucleotides encoding a 22P4F11 protein and fragments thereof, DNA, RNA, DNA/RNA hybrid, and related molecules, polynucleotides or oligonucleotides complementary to a 22P4F11 gene or mRNA sequence or a part thereof, and polynucleotides or oligonucleotides which hybridize to a 22P4F11 gene, mRNA, or to a 22P4F11-encoding polynucleotide (collectively, "22P4F11 polynucleotides"). As used herein, the 22P4F11 gene and protein is meant to include the 22P4F11 genes and proteins specifically described herein and the genes and proteins corresponding to other 22P4F11 proteins and structurally similar variants of the foregoing. Such other 22P4F11 proteins and variants will generally have coding sequences which are highly homologous to the 22P4F11 coding sequence, and preferably will share at least about 50% amino acid identity and at least about 60% amino acid homology (using BLAST criteria), more preferably sharing 70% or greater homology (using BLAST criteria). One embodiment of a 22P4F11 polynucleotide has the sequence shown in FIG. 1A (SEQ ID NO:1).

A 22P4F11 polynucleotide may comprise a polynucleotide having the nucleotide sequence of human 22P4F11 as shown in FIG. 1A (SEQ ID NO:1), wherein T can also be U; a polynucleotide which encodes all or part of the 22P4F11 protein; a sequence complementary to the foregoing; or a polynucleotide fragment of any of the foregoing. Another embodiment comprises a polynucleotide having the sequence as shown in FIG. 1 (SEQ ID NO:1), from nucleotide residue number 236 through nucleotide residue number 1466, wherein T can also be U. Another embodiment comprises a polynucleotide encoding a 22P4F11 polypeptide whose sequence is encoded by the cDNA contained in the plasmid as deposited with American Type Culture Collection as Accession No. 98985. Another embodiment comprises a polynucleotide which is capable of hybridizing under stringent hybridization conditions to the human 22P4F11 cDNA shown in FIG. 1A (SEQ ID NO:1) or to a polynucleotide fragment thereof.

Specifically contemplated are genomic DNA, cDNAs, ribozymes, and antisense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the 22P4F11 polynucleotides and polynucleotide sequences disclosed herein.

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of a 22P4F11 polynucleotide in a sample and as a means for detecting a cell expressing a 22P4F11 protein. Examples of such probes include polypeptides comprising all or part of the human 22P4F11 cDNA sequences shown in FIGS. 1A and 1B. Examples of primer pairs capable of specifically amplifying 22P4F11 mRNAs are also described in the Examples which follow. As will be understood by the skilled artisan, a great many different primers and probes may be prepared based on the sequences provided in herein and used effectively to amplify and/or detect a 22P4F11 mRNA.

As used herein, a polynucleotide is said to be "isolated" when it is substantially separated from contaminant polynucleotides which correspond or are complementary to genes other than the 22P4F11 gene or which encode polypeptides other than 22P4F11 gene product or fragments thereof. A skilled artisan can readily employ nucleic acid isolation procedures to obtain an isolated 22P4F11 polynucleotide.

The 22P4F11 polynucleotides of the invention are useful for a variety of purposes, including but not limited to their use as probes and primers for the amplification and/or detection of the 22P4F11 gene(s), mRNA(s), or fragments thereof; as reagents for the diagnosis and/or prognosis of prostate cancer and other cancers; as coding sequences capable of directing the expression of 22P4F11 polypeptides; as tools for modulating or inhibiting the expression of the 22P4F11 gene(s) and/or translation of the 22P4F11 transcript(s); and as therapeutic agents.

Methods for Isolating 22P4F11-Encoding Nucleic Acid Molecules

The 22P4F11 cDNA sequences described herein enable the isolation of other polynucleotides encoding 22P4F11 gene product(s), as well as the isolation of polynucleotides encoding 22P4F11 gene product homologues, alternatively spliced isoforms, allelic variants, and mutant forms of the 22P4F11 gene product. Various molecular cloning methods that can be employed to isolate full length cDNAs encoding a 22P4F11 gene are well known (See, for example, Sambrook, J. et al., Molecular Cloning: A Laboratory Manual, 2d edition., Cold Spring Harbor Press, New York, 1989; Current Protocols in Molecular Biology. Ausubel et al., Eds., Wiley and Sons, 1995). For example, lambda phage cloning methodologies may be conveniently employed, using commercially available cloning systems (e.g., Lambda ZAP Express, Stratagene). Phage clones containing 22P4F11 gene cDNAs may be identified by probing with a labeled 22P4F11 cDNA or a fragment thereof. For example, in one embodiment, the 22P4F11 cDNA (FIG. 1A, 1B) (SEQ ID NO:1, SEQ ID NO:2) or a portion thereof can be synthesized and used as a probe to retrieve overlapping and full length cDNAs corresponding to a 22P4F11 gene. The 22P4F11 gene itself may be isolated by screening genomic DNA libraries, bacterial artificial chromosome libraries (BACs), yeast artificial chromosome libraries (YACs), and the like, with 22P4F11 DNA probes or primers.

Recombinant DNA Molecules and Host-Vector Systems

The invention also provides recombinant DNA or RNA molecules containing a 22P4F11 polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, for example, Sambrook et al, 1989, supra).

The invention further provides a host-vector system comprising a recombinant DNA molecule containing a 22P4F11 polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such LnCaP, PC-3, DU145, LAPC-4, TsuPr1, other transfectable or transducible prostate cancer cell lines, as well as a number of mammalian cells routinely used for the expression of recombinant proteins (e.g., COS, CHO, 293, 293T cells). More particularly, a polynucleotide comprising the coding sequence of a 22P4F11 may be used to generate 22P4F11 proteins or fragments thereof using any number of host-vector systems routinely used and widely known in the art.

A wide range of host-vector systems suitable for the expression of 22P4F11 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, 22P4F11 may be preferably expressed in several prostate cancer and non-prostate cell lines, including for example 293, 293T, rat-1, 3T3, PC-3, LNCaP and TsuPr1. The host-vector systems of the invention are useful for the production of a 22P4F11 protein or fragment thereof. Such host-vector systems may be employed to study the functional properties of 22P4F11 and 22P4F11 mutations.

Recombinant human 22P4F11 protein may be produced by mammalian cells transfected with a construct encoding 22P4F11. In a particular embodiment described in the Examples, 293T cells are transfected with an expression plasmid encoding 22P4F11, the 22P4F11 protein is expressed in the 293T cells, and the recombinant 22P4F11 protein is isolated using standard purification methods (e.g., affinity purification using anti-22P4F11 antibodies). In another embodiment, also described in the Examples herein, the 22P4F11 coding sequence is subcloned into the retroviral vector pSRαMSVtkneo and used to infect various mammalian cell lines, including 3T3CL7, PC3 and LnCaP in order to establish 22P4F11 expressing cell lines. Various other expression systems well known in the art may also be employed. Expression constructs encoding a leader peptide joined in frame to the 22P4F11 coding sequence may be used for the generation of a secreted form of recombinant 22P4F11 protein.

Proteins encoded by the 22P4F11 genes, or by fragments thereof, will have a variety of uses, including but not limited to generating antibodies and in methods for identifying ligands and other agents (i.e., other bHLH proteins) and cellular constituents that bind to a 22P4F11 gene product. Antibodies raised against a 22P4F11 protein or fragment thereof may be useful in diagnostic and prognostic assays, and imaging methodologies in the management of human cancers characterized by expression of 22P4F11 protein, including but not limited to cancers of the prostate. Such antibodies may be expressed intracellularly and used in methods of treating patients with such cancers. Various immunological assays useful for the detection of 22P4F11 proteins are contemplated, including but not limited to various types of radioimmunoassays, enzyme-linked immunosorbent assays (ELISA), enzyme-linked immunofluorescent assays (ELIFA), immunocytochemical methods, and the like. Such antibodies may be labeled and used as immunological imaging reagents capable of detecting 22P4F11 expressing cells (e.g., in radioscintigraphic imaging methods). 22P4F11 proteins may also be particularly useful in generating cancer vaccines, as further described below.

22P4F11 Proteins

Another aspect of the present invention provides 22P4F11 proteins and polypeptide fragments thereof. The 22P4F11 proteins of the invention include those specifically identified herein, as well as allelic variants, conservative substitution variants and homologs that can be isolated/generated and characterized without undue experimentation following the methods outlined below. Fusion proteins which combine parts of different 22P4F11 proteins or fragments thereof, as well as fusion proteins of a 22P4F11 protein and a heterologous polypeptide are also included. Such 22P4F11 proteins will be collectively referred to as the 22P4F11 proteins, the proteins of the invention, or 22P4F11. As used herein, the term "22P4F11 polypeptide" refers to a polypeptide fragment or a 22P4F11 protein of at least 10 amino acids, preferably at least 15 amino acids.

A specific embodiment of a 22P4F11 protein comprises a polypeptide having the amino acid sequence of human 22P4F11, as shown in FIG. 1A (SEQ ID NO:2).

In general, naturally occurring allelic variants of human 22P4F11 will share a high degree of structural identity and homology (e.g., 90% or more identity). Typically, allelic variants of the 22P4F11 proteins will contain conservative amino acid substitutions within the 22P4F11 sequences described herein or will contain a substitution of an amino acid from a corresponding position in a 22P4F11 homologue. One class of 22P4F11 allelic variants will be proteins that share a high degree of homology with at least a small region of a particular 22P4F11 amino acid sequence, but will further contain a radical departure form the sequence, such as a non-conservative substitution, truncation, insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

22P4F11 proteins may be embodied in many forms, preferably in isolated form. As used herein, a protein is said to be "isolated" when physical, mechanical or chemical methods are employed to remove the 22P4F11 protein from cellular constituents that are normally associated with the protein. A skilled artisan can readily employ standard purification methods to obtain an isolated 22P4F11 protein. A purified 22P4F11 protein molecule will be substantially free of other proteins or molecules which impair the binding of 22P4F11 to antibody or other ligand. The nature and degree of isolation and purification will depend on the intended use. Embodiments of a 22P4F11 protein include a purified 22P4F11 protein and a functional, soluble 22P4F11 protein. In one form, such functional, soluble 22P4F11 proteins or fragments thereof retain the ability to bind antibody or other ligand.

The invention also provides 22P4F11 polypeptides comprising biologically active fragments of the 22P4F11 amino acid sequence, such as a polypeptide corresponding to part of the amino acid sequences for 22P4F11 as shown in FIG. 1A (SEQ ID NO:2). Such polypeptides of the invention exhibit properties of the 22P4F11 protein, such as the ability to elicit the generation of antibodies which specifically bind an epitope associated with the 22P4F11 protein.

22P4F11 polypeptides can be generated using standard peptide synthesis technology or using chemical cleavage methods well known in the art based on the amino acid sequences of the human 22P4F11 proteins disclosed herein. Alternatively, recombinant methods can be used to generate nucleic acid molecules that encode a polypeptide fragment of a 22P4F11 protein. In this regard, the 22P4F11-encoding nucleic acid molecules described herein provide means for generating defined fragments of 22P4F11 proteins. 22P4F11 polypeptides are particularly useful in generating and characterizing domain specific antibodies (e.g., antibodies recognizing an extracellular or intracellular epitope of a 22P4F11 protein), in identifying agents or cellular factors that bind to 22P4F11 or a particular structural domain thereof, and in various therapeutic contexts, including but not limited to cancer vaccines.

Polypeptides comprising amino acid sequences which are unique to a particular 22P4F11 protein (relative to other 22P4F11 proteins) may be used to generate antibodies which will specifically react with that particular 22P4F11 protein.

22P4F11 polypeptides containing particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments containing such structures are particularly useful in generating subunit specific anti-22P4F11 antibodies or in identifying cellular factors that bind to 22P4F11.

In a specific embodiment described in the examples which follow, 22P4F11 is conveniently expressed in 293T cells transfected with a CMV-driven expression vector encoding 22P4F11 with a C-terminal 6×His and MYC tag (pcDNA3.1/mycHIS, Invitrogen). The secreted HIS-tagged 22P4F11 in the culture media may be purified using a nickel column using standard techniques.

22P4F11 Antibodies

Another aspect of the invention provides antibodies that bind to 22P4F11 proteins and polypeptides. The most preferred antibodies will specifically bind to a 22P4F11 protein and will not bind (or will bind weakly) to non-22P4F11 proteins and polypeptides. Anti-22P4F11 antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule which binds to its target, i.e., the antigen binding region.

22P4F11 antibodies of the invention may be particularly useful in prostate cancer diagnostic and prognostic assays, and imaging methodologies. Intracellularly expressed antibodies (e.g., single chain antibodies) may be therapeutically useful in treating cancers in which the expression of 22P4F11 is involved, such as for example advanced and metastatic prostate cancers. Similarly, such antibodies may be useful in the treatment, diagnosis, and/or prognosis of other cancers, to the extent 22P4F11 is also expressed or overexpressed in other types of cancer.

The invention also provides various immunological assays useful for the detection and quantification of 22P4F11 and mutant 22P4F11 proteins and polypeptides. Such assays generally comprise one or more 22P4F11 antibodies capable of recognizing and binding a 22P4F11 or mutant 22P4F11 protein, as appropriate, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting prostate cancer and other cancers expressing 22P4F11 are also provided by the invention, including but limited to radioscintigraphic imaging methods using labeled 22P4F11 antibodies. Such assays may be clinically useful in the detection, monitoring, and prognosis of 22P4F11 expressing cancers such as prostate cancer.

22P4F11 antibodies may also be used in methods for purifying 22P4F11 and mutant 22P4F11 proteins and polypeptides and for isolating 22P4F11 homologues and related molecules. For example, in one embodiment, the method of purifying a 22P4F11 protein comprises incubating a 22P4F11 antibody, which has been coupled to a solid matrix, with a lysate or other solution containing 22P4F11 under conditions which permit the 22P4F11 antibody to bind to 22P4F11; washing the solid matrix to eliminate impurities; and eluting the 22P4F11 from the coupled antibody. Other uses of the 22P4F11 antibodies of the invention include generating anti-idiotypic antibodies that mimic the 22P4F11 protein.

Various methods for the preparation of antibodies are well known in the art. For example, antibodies may be prepared by immunizing a suitable mammalian host using a 22P4F11 protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of 22P4F11 may also be used, such as a 22P4F11 GST-fusion protein. In a particular embodiment, a GST fusion protein comprising all or most of the open reading frame amino acid sequence of FIG. 1A (SEQ ID NO:2) may be produced and used as an immunogen to generate appropriate antibodies. In another embodiment, a 22P4F11 peptide may be synthesized and used as an immunogen.

In addition, naked DNA immunization techniques known in the art may be used (with or without purified 22P4F11 protein or 22P4F11 expressing cells) to generate an immune response to the encoded immunogen (for review, see Donnelly et al., 1997, Ann. Rev. Immunol. 15: 617-648).

The amino acid sequence of the 22P4F11 as shown in FIG. 1A (SEQ ID NO:2) may be used to select specific regions of the 22P4F11 protein for generating antibodies. For example, hydrophobicity and hydrophilicity analyses of the 22P4F11 amino acid sequence may be used to identify hydrophilic regions in the 22P4F11 structure. Regions of the 22P4F11 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Methods for the generation of 22P4F11 antibodies are further illustrated by way of the examples provided herein.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a 22P4F11 immunogen is conducted generally by injection over a suitable time period and with use of a suitable adjuvant, as is generally understood in the art. During the immunization schedule, titers of antibodies can be taken to determine adequacy of antibody formation.

22P4F11 monoclonal antibodies are preferred and may be produced by various means well known in the art. For example, immortalized cell lines which secrete a desired monoclonal antibody may be prepared using the standard hybridoma technology of Kohler and Milstein or modifications which immortalize producing B cells, as is generally known. The immortalized cell lines secreting the desired antibodies are screened by immunoassay in which the antigen is the 22P4F11 protein or a 22P4F11 fragment. When the appropriate immortalized cell culture secreting the desired antibody is identified, the cells may be expanded and antibodies produced either from in vitro cultures or from ascites fluid.

The antibodies or fragments may also be produced, using current technology, by recombinant means. Regions that bind specifically to the desired regions of the 22P4F11 protein can also be produced in the context of chimeric or CDR grafted antibodies of multiple species origin. Humanized or human 22P4F11 antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321: 522-525; Riechmnan et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296. Methods for producing fully human monoclonal antibodies include phage display and transgenic methods (for review, see Vaughan et al., 1998, Nature Biotechnology 16: 535-539).

Fully human 22P4F11 monoclonal antibodies may be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45-64 (1993); Burton and Barbas, Human Antibodies from combinatorial libraries. Id., pp 65-82). Fully human 22P4F11 monoclonal antibodies may also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607-614). This method avoids the in vitro manipulation required with phage display technology and efficiently produces high affinity authentic human antibodies.

Reactivity of 22P4F11 antibodies with a 22P4F11 protein may be established by a number of well known means, including Western blot, immunoprecipitation, ELISA, and FACS analyses using, as appropriate, 22P4F11 proteins, peptides, 22P4F11-expressing cells or extracts thereof.

A 22P4F11 antibody or fragment thereof of the invention may be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 22P4F11 epitopes may be generated using methods generally known in the art. Homodimeric antibodies may also be generated by cross-linking techniques known in the art (e.g., Wolff et al., Cancer Res. 53: 2560-2565).

Methods for the Detection of 22P4F11

Another aspect of the present invention relates to methods for detecting 22P4F11 polynucleotides and 22P4F11 proteins, as well as methods for identifying a cell which expresses 22P4F11.

More particularly, the invention provides assays for the detection of 22P4F11 polynucleotides in a biological sample, such as serum, bone, prostate, and other tissues, urine, semen, cell preparations, and the like. Detectable 22P4F11 polynucleotides include, for example, a 22P4F11 gene or fragments thereof, 22P4F11 mRNA, alternative splice variant 22P4F11 mRNAs, and recombinant DNA or RNA molecules containing a 22P4F11 polynucleotide. A number of methods for amplifying and/or detecting the presence of 22P4F11 polynucleotides are well known in the art and may be employed in the practice of this aspect of the invention.

In one embodiment, a method for detecting a 22P4F11 mRNA in a biological sample comprises producing cDNA from the sample by reverse transcription using at least one primer; amplifying the cDNA so produced using a 22P4F11 polynucleotides as sense and antisense primers to amplify 22P4F11 cDNAs therein; and detecting the presence of the amplified 22P4F11 cDNA. In another embodiment, a method of detecting a 22P4F11 gene in a biological sample comprises first isolating genomic DNA from the sample; amplifying the isolated genomic DNA using 22P4F11 polynucleotides as sense and antisense primers to amplify the 22P4F11 gene therein; and detecting the presence of the amplified 22P4F11 gene. Any number of appropriate sense and antisense probe combinations may be designed from the nucleotide sequences provided for the 22P4F11 (FIGS. 1 and 2) (SEQ ID NOS: 1 and 3) and used for this purpose.

The invention also provides assays for detecting the presence of a 22P4F11 protein in a tissue of other biological sample such as serum, bone, prostate, and other tissues, urine, cell preparations, and the like. Methods for detecting a 22P4F11 protein are also well known and include, for example, immunoprecipitation, immunohistochemical analysis, Western Blot analysis, molecular binding assays, ELISA, ELIFA and the like. For example, in one embodiment, a method of detecting the presence of a 22P4F11 protein in a biological sample comprises first contacting the sample with a 22P4F11 antibody, a 22P4F11-reactive fragment thereof, or a recombinant protein containing an antigen binding region of a 22P4F11 antibody; and then detecting the binding of 22P4F11 protein in the sample thereto.

Methods for identifying a cell which expresses 22P4F11 are also provided. In one embodiment, an assay for identifying a cell which expresses a 22P4F11 gene comprises detecting the presence of 22P4F11 mRNA in the cell. Methods for the detection of particular mRNAs in cells are well known and include, for example, hybridization assays using complementary DNA probes (such as in situ hybridization using labeled 22P4F11 riboprobes, Northern blot and related techniques) and various nucleic acid amplification assays (such as RT-PCR using complementary primers specific for 22P4F11, and other amplification type detection methods, such as, for example, branched DNA, SISBA, TMA and the like). Alternatively, an assay for identifying a cell which expresses a 22P4F11 gene comprises detecting the presence of 22P4F11 protein in the cell or secreted by the cell. Various methods for the detection of proteins are well known in the art and may be employed for the detection of 22P4F11 proteins and 22P4F11 expressing cells.

22P4F11 expression analysis may also be useful as a tool for identifying and evaluating agents which modulate 22P4F11 gene expression. For example, 22P4F11 expression is significantly upregulated in prostate cancer, and may also be expressed in other cancers. Identification of a molecule or biological agent that could inhibit 22P4F11 expression or over-expression in cancer cells may be of therapeutic value. Such an agent may be identified by using a screen that quantifies 22P4F11 expression by RT-PCR, nucleic acid hybridization or antibody binding.

Assays for Determining 22P4F11 Expression Status

Determining the status of 22P4F11 expression patterns in an individual may be used to diagnose cancer and may provide prognostic information useful in defining appropriate therapeutic options. Similarly, the expression status of 22P4F11 may provide information useful for predicting susceptibility to particular disease stages, progression, and/or tumor aggressiveness. The invention provides methods and assays for determining 22P4F11 expression status and diagnosing cancers which express 22P4F11, such as cancers of the prostate. 22P4F11 expression status in patient samples may be analyzed by a number of means well known in the art, including without limitation, immunohistochemical analysis, in situ hybridization, RT-PCR analysis on laser capture micro-dissected samples, western blot analysis of clinical samples and cell lines, and tissue array analysis.

In one aspect, the invention provides assays useful in determining the presence of cancer in an individual, comprising detecting a significant increase in 22P4F11 mRNA or protein expression in a test cell or tissue sample relative to expression levels in the corresponding normal cell or tissue. The presence of 22P4F11 mRNA may, for example, be evaluated in tissue samples including but not limited to colon, lung, prostate, pancreas, bladder, breast, ovary, cervix, testis, head and neck, brain, stomach, etc. The presence of significant 22P4F11 expression in any of these tissues may be useful to indicate the emergence, presence and/or severity of these cancers, since the corresponding normal tissues do not express 22P4F11 mRNA or express it at lower levels.

In a related embodiment, 22P4F11 expression status may be determined at the protein level rather than at the nucleic acid level. For example, such a method or assay would comprise determining the level of 22P4F11 protein expressed by cells in a test tissue sample and comparing the level so determined to the level of 22P4F11 expressed in a corresponding normal sample. In one embodiment, the presence of 22P4F11 protein is evaluated, for example, using immunohistochemical methods. 22P4F11 antibodies or binding partners capable of detecting 22P4F11 protein expression may be used in a variety of assay formats well known in the art for this purpose.

In addition, peripheral blood may be conveniently assayed for the presence of cancer cells, including but not limited to prostate cancers, using RT-PCR to detect 22P4F11 expression. The presence of RT-PCR amplifiable 22P4F11 mRNA provides an indication of the presence of the cancer. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25: 373-384; Ghossein et al., 1995, J. Clin. Oncol. 13: 1195-2000; Heston et al., 1995, Clin. Chem. 41: 1687-1688). RT-PCR assays are well known in the art.

A related aspect of the invention is directed to predicting susceptibility to developing cancer in an individual. In one embodiment, a method for predicting susceptibility to cancer comprises detecting 22P4F11 mRNA or 22P4F11 protein in a tissue sample, its presence indicating susceptibility to cancer, wherein the degree of 22P4F11 mRNA expression present is proportional to the degree of susceptibility. In a specific embodiment, the presence of 22P4F11 in prostate tissue is examined, with the presence of 22P4F11 in the sample providing an indication of prostate cancer susceptibility (or the emergence or existence of a prostate tumor).

Yet another related aspect of the invention is directed to methods for gauging tumor aggressiveness. In one embodiment, a method for gauging aggressiveness of a tumor comprises determining the level of 22P4F11 mRNA or 22P4F11 protein expressed by cells in a sample of the tumor, comparing the level so determined to the level of 22P4F11 mRNA or 22P4F11 protein expressed in a corresponding normal tissue taken from the same individual or a normal tissue reference sample, wherein the degree of 22P4F11 mRNA or 22P4F11 protein expression in the tumor sample relative to the normal sample indicates the degree of aggressiveness. In a specific embodiment, aggressiveness of prostate tumors is evaluated by determining the extent to which 22P4F11 is expressed in the tumor cells, with higher expression levels indicating more aggressive tumors.

Methods for detecting and quantifying the expression of 22P4F11 mRNA or protein are described herein and use standard nucleic acid and protein detection and quantification technologies well known in the art. Standard methods for the detection and quantification of 22P4F11 mRNA include in situ hybridization using labeled 22P4F11 riboprobes, Northern blot and related techniques using 22P4F11 polynucleotide probes, RT-PCR analysis using primers specific for 22P4F11, and other amplification type detection methods, such as, for example, branched DNA, SISBA, TMA and the like. In a specific embodiment, semi-quantitative RT-PCR may be used to detect and quantify 22P4F11 mRNA expression as described in the Examples which follow. Any number of primers capable of amplifying 22P4F11 may be used for this purpose, including but not limited to the various primer sets specifically described herein. Standard methods for the detection and quantification of protein may be used for this purpose. In a specific embodiment, polyclonal or monoclonal antibodies specifically reactive with the wild-type 22P4F11 protein may be used in an immunohistochemical assay of biopsied tissue.

Therapeutic Methods and Compositions

The identification of 22P4F11 as a normally testis-specific protein that is also expressed in cancers of the prostate (and possibly other cancers), opens a number of therapeutic approaches to the treatment of such cancers.

Accordingly, therapeutic approaches aimed at inhibiting the activity of the 22P4F11 protein are expected to be useful for patients suffering from prostate cancer and other cancers expressing 22P4F11. These therapeutic approaches generally fall into two classes. In this regard, a variety of methods for inhibiting the transcription of the 22P4F11 gene or translation of 22P4F11 mRNA may be employed.

A. Therapeutic Inhibition of 22P4F11 with Intracellular Antibodies

Recombinant vectors encoding single chain antibodies which specifically bind to 22P4F11 may be introduced into 22P4F11 expressing cells via gene transfer technologies, wherein the encoded single chain anti-22P4F11 antibody is expressed intracellularly, binds to 22P4F11 protein, and thereby inhibits its function. Methods for engineering such intracellular single chain antibodies are well known. Such intracellular antibodies, also known as "intrabodies", may be specifically targeted to a particular compartment within the cell, providing control over where the inhibitory activity of the treatment will be focused. This technology has been successfully applied in the art (for review, see Richardson and Marasco, 1995, TIBTECH vol. 13). Intrabodies have been shown to virtually eliminate the expression of otherwise abundant cell surface receptors. See, for example, Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337.

Single chain antibodies comprise the variable domains of the heavy and light chain joined by a flexible linker polypeptide, and are expressed as a single polypeptide. Optionally, single chain antibodies may be expressed as a single chain variable region fragment joined to the light chain constant region. Well known intracellular trafficking signals may be engineered into recombinant polynucleotide vectors encoding such single chain antibodies in order to precisely target the expressed intrabody to the desired intracellular compartment. For example, intrabodies targeted to the endoplasmic reticulum (ER) may be engineered to incorporate a leader peptide and, optionally, a C-terminal ER retention signal, such as the KDEL amino acid motif. Intrabodies intended to exert activity in the nucleus may be engineered to include a nuclear localization signal. Lipid moieties may be joined to intrabodies in order to tether the intrabody to the cytosolic side of the plasma membrane. Intrabodies may also be targeted to exert function in the cytosol. For example, cytosolic intrabodies may be used to sequester factors within the cytosol, thereby preventing them from being transported to their natural cellular destination.

In order to specifically direct the expression of such intrabodies to particular tumor cells, the transcription of the intrabody may be placed under the regulatory control of an appropriate tumor-specific promoter and/or enhancer. In order to target intrabody expression specifically to prostate, for example, the PSA promoter and/or promoter/enhancer may be utilized (See, for example, U.S. Pat. No. 5,919,652).

B. Therapeutic Methods Based on Inhibition of 22P4F11 Transcription or Translation Also provided are various methods and compositions for inhibiting the transcription of the 22P4F11 gene. Similarly, the invention also provides methods and compositions for inhibiting the translation of 22P4F11 mRNA into protein.

In one approach, a method of inhibiting the transcription of the 22P4F11 gene comprises contacting the 22P4F11 gene with a 22P4F11 antisense polynucleotide. In another approach, a method of inhibiting 22P4F11 mRNA translation comprises contacting the 22P4F11 mRNA with an antisense polynucleotide. In another approach, a 22P4F11 specific ribozyme may be used to cleave the 22P4F11 message, thereby inhibiting translation. Such antisense and ribozyme based methods may also be directed to the regulatory regions of the 22P4F11 gene, such as the 22P4F11 promoter and/or enhancer elements. Similarly, proteins capable of inhibiting a 22P4F11 gene transcription factor may be used to inhibit 22P4F11 mRNA transcription. The various polynucleotides and compositions useful in the aforementioned methods have been described above. The use of antisense and ribozyme molecules to inhibit transcription and translation is well known in the art.

Other factors which inhibit the transcription of 22P4F11 through interfering with 22P4F11 transcriptional activation may also be useful for the treatment of cancers expressing 22P4F11. Similarly, factors which are capable of interfering with 22P4F11 processing may be useful for the treatment of cancers expressing 22P4F11. Cancer treatment methods utilizing such factors are also within the scope of the invention.

C. General Considerations

Gene transfer and gene therapy technologies may be used for delivering therapeutic polynucleotide molecules to tumor cells synthesizing 22P4F11 (i.e., antisense, ribozyme, polynucleotides encoding intrabodies and other 22P4F11 inhibitory molecules). A number of gene therapy approaches are known in the art. Recombinant vectors encoding 22P4F11 antisense polynucleotides, ribozymes, factors capable of interfering with 22P4F11 transcription, and so forth, may be delivered to target tumor cells using such gene therapy approaches.

The above therapeutic approaches may be combined with chemotherapy or radiation therapy regimens. These therapeutic approaches may also enable the use of reduced dosages of chemotherapy and/or less frequent administration, particularly in patients that do not tolerate the toxicity of the chemotherapeutic agent well.

The anti-tumor activity of a particular composition (e.g., antisense, ribozyme, intrabody), or a combination of such compositions, may be evaluated using various in vitro and in vivo assay systems. In vitro assays for evaluating therapeutic potential include cell growth assays, soft agar assays and other assays indicative of tumor promoting activity, binding assays capable of determining the extent to which a therapeutic composition will inhibit the binding of 22P4F11 to a binding partner, etc.

In vivo, the effect of a 22P4F11 therapeutic composition may be evaluated in a suitable animal model. For example, xenogenic prostate cancer models wherein human prostate cancer explants or passaged xenograft tissues are introduced into immune compromised animals, such as nude or SCID mice, are appropriate in relation to prostate cancer and have been described (Klein et al., 1997, Nature Medicine 3: 402-408). For Example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy may be predicted using assays which measure inhibition of tumor formation, tumor regression or metastasis, and the like. See, also, the Examples below.

In vivo assays which qualify the promotion of apoptosis may also be useful in evaluating potential therapeutic compositions. In one embodiment, xenografts from bearing mice treated with the therapeutic composition may be examined for the presence of apoptotic foci and compared to un-treated control xenograft-bearing mice. The extent to which apoptotic foci are found in the tumors of the treated mice provides an indication of the therapeutic efficacy of the composition.

The therapeutic compositions used in the practice of the foregoing methods may be formulated into pharmaceutical compositions comprising a carrier suitable for the desired delivery method. Suitable carriers include any material which when combined with the therapeutic composition retains the anti-tumor function of the therapeutic composition and is non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16th Edition, A. Osal., Ed., 1980).

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations may be lyophilized and stored as sterile powders, preferably under vacuum, and then reconstituted in bacteriostatic water containing, for example, benzyl alcohol preservative, or in sterile water prior to injection.

Dosages and administration protocols for the treatment of cancers using the foregoing methods will vary with the method and the target cancer and will generally depend on a number of other factors appreciated in the art.

Cancer Vaccines

The invention further provides prostate cancer vaccines comprising a 22P4F11 protein or fragment thereof, as well as DNA based vaccines. In view of the testis-restricted expression of 22P4F11 in normal human tissues (and the existence of the testis-blood barrier), 22P4F11 cancer vaccines are expected to be effective at specifically preventing and/or treating 22P4F11 expressing cancers without creating non-specific effects on non-target tissues. The use of a tumor antigen in a vaccine for generating humoral and cell-mediated immunity for use in anti-cancer therapy is well known in the art and has been employed in prostate cancer using human PSMA and rodent PAP immunogens (Hodge et al., 1995, Int. J. Cancer 63: 231-237; Fong et al., 1997, J. Immunol. 159: 3113-3117). Such methods can be readily practiced by employing a 22P4F11 protein, or fragment thereof, or a 22P4F11-encoding nucleic acid molecule and recombinant vectors capable of expressing and appropriately presenting the 22P4F11 immunogen.

For example, viral gene delivery systems may be used to deliver a 22P4F11-encoding nucleic acid molecule. Various viral gene delivery systems which can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658-663). Non-viral delivery systems may also be employed by using naked DNA encoding a 22P4F11 protein or fragment thereof introduced into the patient (e.g., intramuscularly) to induce an anti-tumor response. In one embodiment, the full-length human 22P4F11 cDNA may be employed. In another embodiment, 22P4F11 nucleic acid molecules encoding specific cytotoxic T lymphocyte (CTL) epitopes may be employed. CTL epitopes can be determined using specific algorithms (e.g., Epimer, Brown University) to identify peptides within a 22P4F11 protein which are capable of optimally binding to specified HLA alleles.

Various ex vivo strategies may also be employed. One approach involves the use of dendritic cells to present 22P4F11 antigen to a patient's immune system. Dendritic cells express MHC class I and II, B7 costimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28: 65-69; Murphy et al., 1996, Prostate 29: 371-380). Dendritic cells can be used to present 22P4F11 peptides to T cells in the context of MHC class I and II molecules. In one embodiment, autologous dendritic cells are pulsed with 22P4F11 peptides capable of binding to MHC molecules. In another embodiment, dendritic cells are pulsed with the complete 22P4F11 protein. Yet another embodiment involves engineering the overexpression of the 22P4F11 gene in dendritic cells using various implementing vectors known in the art, such as adenovirus (Arthur et al., 1997, Cancer Gene Ther. 4: 17-25), retrovirus (Henderson et al., 1996, Cancer Res. 56: 3763-3770), lentivirus, adeno-associated virus, DNA transfection (Ribas et al., 1997, Cancer Res. 57: 2865-2869), and tumor-derived RNA transfection (Ashley et al., 1997, J. Exp. Med. 186: 1177-1182). Cells expressing 22P4F11 may also be engineered to express immune modulators, such as GM-CSF, and used as immunizing agents.

Anti-idiotypic anti-22P4F11 antibodies can also be used in anti-cancer therapy as a vaccine for inducing an immune response to cells expressing a 22P4F11 protein. Specifically, the generation of anti-idiotypic antibodies is well known in the art and can readily be adapted to generate anti-idiotypic anti-22P4F11 antibodies that mimic an epitope on a 22P4F11 protein (see, for example, Wagner et al., 1997, Hybridoma 16: 33-40; Foon et al., 1995, J Clin Invest 96: 334-342; Herlyn et al., 1996, Cancer Immunol Immunother 43: 65-76). Such an anti-idiotypic antibody can be used in cancer vaccine strategies.

Genetic immunization methods may be employed to generate prophylactic or therapeutic humoral and cellular immune responses directed against cancer cells expressing 22P4F11. Constructs comprising DNA encoding a 22P4F11 protein/immunogen and appropriate regulatory sequences may be injected directly into muscle or skin of an individual, such that the cells of the muscle or skin take-up the construct and express the encoded 22P4F11 protein/immunogen. Expression of the 22P4F11 protein immunogen results in the generation of prophylactic or therapeutic humoral and cellular immunity against prostate cancer. Various prophylactic and therapeutic genetic immunization techniques known in the art may be used.

Kits

For use in the diagnostic and therapeutic applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe which is or can be detectably labeled. Such probe may be an antibody or polynucleotide specific for a 22P4F11 protein or a 22P4F11 gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

EXAMPLES

Various aspects of the invention are further described and illustrated by way of the several examples which follow, none of which are intended to limit the scope of the invention.

Example 1

SSH-Generated Isolation of cDNA Fragment of the 22P4F11 Gene

Materials and Methods

LAPC Xenografts:

LAPC xenografts were obtained from Dr. Charles Sawyers (UCLA) and generated as described (Klein et al, 1997, Nature Med. 3: 402-408). Androgen dependent and independent LAPC-4 xenografts LAPC-4 AD and AI, respectively) and LAPC-9 AD xenografts were grown in male SCID mice and were passaged as small tissue chunks in recipient males. LAPC-4 AI xenografts were derived from LAPC-4 AD tumors. Male mice bearing LAPC-4 AD tumors were castrated and maintained for 2-3 months. After the LAPC-4 tumors re-grew, the tumors were harvested and passaged in castrated males or in female SCID mice.

Cell Lines:

Human cell lines (e.g., HeLa) were obtained from the ATCC and were maintained in DMEM with 5% fetal calf serum.

RNA Isolation:

Tumor tissue and cell lines were homogenized in Trizol reagent (Life Technologies, Gibco BRL) using 10 ml/g tissue or 10 ml/108 cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.

```
DPNCDN (cDNA synthesis primer):       (SEQ ID NO: 5)
5'TTTT GATCAAGCTT303'

Adaptor 1:                            (SEQ ID NO: 6)
5'CTAATACGACTCACTATAGGGCTCGAGCGGCCGCCCGGGCAG3'

3'GGCCCGTCCTAG5'                       (SEQ ID NO: 15)

Adaptor 2:                            (SEQ ID NO: 7)
5'GTAATACGACTCACTATAGGGCAGCGTGGTCGCGGCCGAG3'

3'CGGCTCCTAG5'                         (SEQ ID NO: 16)

PCR primer 1:                         (SEQ ID NO: 8)
5'CTAATACGACTCACTATAGGGC3'

Nested primer (NP)1:                  (SEQ ID NO: 9)
5'TCGAGCGGCCGCCCGGGCAGGA3'

Nested primer (NP)2:                  (SEQ ID NO: 10)
5'AGCGTGGTCGCGGCCGAGGA3'
```

Suppression Subtractive Hybridization:

Suppression Subtractive Hybridization (SSH) was used to identify cDNAs corresponding to genes which may be differentially expressed in prostate cancer.

Double stranded cDNAs corresponding to the LAPC-4 AI xenograft (tester) and the LAPC-4 AD xenograft (driver) were synthesized from 2 µg of poly(A)+RNA isolated from xenograft tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs. at 37° C. Digested cDNA was extracted with phenol/chloroform (1:1) and ethanol precipitated.

Driver cDNA (LAPC-4 AD) was generated by combining in a 1:1 ratio Dpn II digested LAPC-4 AD cDNA with a mix of digested cDNAs derived from human benign prostatic hyperplasia (BPH), the human cell lines HeLa, 293, A431, Colo205, and mouse liver.

Tester cDNA (LAPC-4 AI) was generated by diluting 1 µl of Dpn II digested LAPC-4 AI cDNA (400 ng) in 5 µl of water. The diluted cDNA (2 µl, 160 ng) was then ligated to 2 µl of Adaptor 1 and Adaptor 2 (10 µM), in separate ligation reactions, in a total volume of 10 µl at 16° C. overnight, using 400 u of T4 DNA ligase (CLONTECH). Ligation was terminated with 1 µl of 0.2 M EDTA and heating at 72° C. for 5 min.

The first hybridization was performed by adding 1.5 µl (600 ng) of driver cDNA to each of two tubes containing 1.5 µl (20 ng) Adaptor 1- and Adaptor 2-ligated tester cDNA. In a final volume of 4 µl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 µl of fresh denatured driver cDNA and were allowed to hybridize overnight at 68° C. The second hybridization was then diluted in 200 µl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 µl of the diluted final hybridization mix was added to 1 µl of PCR primer 1 (10 µM), 0.5 µl dNTP mix (10 µM), 2.5 µl 10× reaction buffer (CLONTECH) and 0.5 µl 50× Advantage cDNA polymerase Mix (CLONTECH) in a final volume of 25 µl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 µl from the pooled and diluted primary PCR reaction was added to the same reaction mix as used for PCR 1, except that primers NP1 and NP2 (10 µM) were used instead of PCR primer 1. PCR 2 was performed using 10-12 cycles of 94° C. for 10 sec, 68° C. for 30 sec, 72° C. for 1.5 minutes. The PCR products were analyzed using 2% agarose gel electrophoresis.

The PCR products were inserted into pCR2.1 using the T/A vector cloning kit (Invitrogen). Transformed E. coli were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis:

First strand cDNAs were generated from 1 µg of mRNA with oligo (dT)12 18 priming using the Gibco BRL Superscript Preamplification system. The manufacturers protocol was used and included an incubation for 50 min at 42° C. with reverse transcriptase followed by RNAse H treatment at 37°

C. for 20 min. After completing the reaction, the volume was increased to 200 µl with water prior to normalization. First strand cDNAs from 16 different normal human tissues were obtained from Clontech.

Normalization of the first strand cDNAs from multiple tissues was performed by using the primers 5'atatcgc-cgcgctcgtcgtcgacaa3' (SEQ ID NO:13) and 5'agccacacg-cagctcattgtagaagg 3' (SEQ ID NO:14) to amplify β-actin. First strand cDNA (5 µl) was amplified in a total volume of 50 µl containing 0.4 µM primers, 0.2 µM each dNTPs, 1×PCR buffer (Clontech, 10 mM Tris HCL, 1.5 mM $MgCl_2$, 50 mM KCl, pH8.3) and 1× Klentaq DNA polymerase (Clontech). Five pt of the PCR reaction was removed at 18, 20, and 22 cycles and used for agarose gel electrophoresis. PCR was performed using an MJ Research thermal cycler under the following conditions: initial denaturation was at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization were required to achieve equal band intensities in all tissues after 22 cycles of PCR.

To determine expression levels of the 22P4F11 gene, 5 µl of normalized first strand cDNA was analyzed by PCR using 25, 30, and 35 cycles of amplification using the following primer pairs, which were designed with the assistance of MIT:

```
                                        (SEQ ID NO: 1)
5'- GCC ACA AAC AGA ATG CAA TGA AAG -3'

(SEQ ID NO: 12)
5'- AAA CTG CCT GTG GTG AAA GTA GA -3'
```

Semi quantitative expression analysis was achieved by comparing the PCR products at cycle numbers that give light band intensities.

Results:

The SSH experiment described in the Materials and Methods, supra, led to the isolation of numerous candidate gene fragment clones (SSH clones). All candidate clones were sequenced and subjected to homology analysis against all sequences in the major public gene and EST databases in order to provide information on the identity of the corresponding gene and to help guide the decision to analyze a particular gene for differential expression. In general, gene fragments which had no homology to any known sequence in any of the searched databases, and thus considered to represent novel genes, as well as gene fragments showing homology to previously sequenced expressed sequence tags (ESTs), were subjected to differential expression analysis by RT-PCR and/or Northern analysis.

One of the SHH clones comprising about 209 bp, showed no homology to any known gene, and was designated 22P4F11. The nucleotide sequence of this SHH clone is shown in FIG. 1B (SEQ ID NO:3). This partial cDNA sequence of the 22P4F11 gene encodes an open reading frame of 69 amino acids. Differential expression analysis by RT-PCR showed expression in all LAPC xenografts and in normal prostate at approximately equal levels (FIG. 2, Panel A). In addition, further RT-PCR expression analysis of first strand cDNAs from 16 normal tissues detected high level expression of the 22P4F11 gene only in prostate, testis, lung and liver (FIG. 2, panels B and C).

Example 2

Isolation of Full Length cDNA Encoding the 22P4F11 Gene

The 22P4F11 SSH fragment (Example 1) was used to isolate additional cDNAs encoding this gene. Briefly, a normal human prostate cDNA library (Clontech) was screened with a labeled probe generated from the 22P4F11 cDNA. One of the positive clones, clone GTP3E10, was 2250 by in length, and encoded the entire open reading frame of the 22P4F11 gene. The 22P4F11-GTP3E10 cDNA encodes a 387 amino acid protein and contains a predicted mitochondrial signal sequence. The 22P4F11-GTP3E10 cDNA was deposited as plasmid p22P4F11-GTP3E10 with the American Type Culture Collection (ATCC) at 10801 University Boulevard, Mannassas, Va., an International Depository Authority under the provisions of the Budapest Treaty, on Nov. 11, 1998. It has been accorded ATCC Accession Number 98985. All restrictions upon public access to the deposit will be irrevocably removed upon the grant of a patent on this application, and the deposit will be replaced if viable samples cannot be dispensed by the depository. The material has been deposited under conditions that ensure that access to the material will be available during the pendency of the patent application to one determined by the Commissioner to be entitled thereto under 35 C.F.R. §1.14 and 35 U.S.C. §122. The deposited material will be stored with all care necessary to keep it viable and uncontaminated for a period of at least five years after the most recent request for the furnishing of a sample of the deposited material, and in any case at least thirty (30) years after the date of a deposit or for the enforceable life of the patent, whichever is longer. The nucleotide and deduced amino acid sequences of the 22P4F11 gene encoded by this cDNA are shown in FIG. 1A (SEQ ID NOS: 1 and 2, respectively).

Example 3

Northern Blot Analysis of 22P4F11 RNA Expression

22P4F11 mRNA expression in normal human tissues was conducted by Northern blotting two multiple tissue blots obtained from Clontech (Palo Alto, Calif.), comprising a total of 16 different normal human tissues, using labeled 22P4F11-GTP3E10 cDNA as a probe. RNA samples were quantitatively normalized with a β-actin probe. The results are shown in FIGS. 3A&B. Expression was only detected in testis.

To analyze 22P4F11 expression in human cancer tissues and cell lines, RNAs derived from human prostate cancer xenografts, normal prostate and a prostate cancer cell line were also analyzed. The results are shown in FIG. 3C. Strong expression was detected in one of the LAPC-4 xenografts, and lower level expression was detected in the LNCaP prostate cancer cell line and in some of the other xenografts. No message was detected in normal prostate.

Example 4

Generation of 22P4F11 Polyclonal Antibodies

To generate polyclonal antibodies directed against 22P4F11 a peptide corresponding to a predicted antigenic sequence is designed from a coding region of the 22P4F11 protein (FIG. 1A) (SEQ ID NO:2). The peptide is then conjugated to keyhole limpet hemocyanin (KLH) and was used to immunize a rabbit.

To test the rabbit serum for reactivity with 22P4F11 proteins, full length 22P4F11 and 22P4F11 cDNAs are cloned into an expression vector that provides a 6H is tag at the carboxyl-terminus (pCDNA 3.1 myc-his, InVitrogen). After transfection of the constructs into 293T cells, cell lysates are probed with anti-His antibody (Santa Cruz) and the anti-22P4F11 serum using Western blotting.

Example 5

Production of Recombinant 22P4F11 in a Mammalian Systems

To express recombinant 22P4F11, the full length 22P4F11 cDNA is cloned into an expression vector that provides a 6H is tag at the carboxyl-terminus (pCDNA 3.1 myc-his, InVitrogen). The construct is transfected into 293T cells. Transfected 293T cell lysates are probed with anti-22P4F11 polyclonal serum prepared, as described in Example 5 above, in a Western blot.

The 22P4F11 genes are subcloned into the retroviral expression vector pSRαMSVtkneo and used to establish 22P4F11 expressing cell lines as follows. The 22P4F11 coding sequence (from translation initiation ATG to the termination codons) is amplified by PCR using ds cDNA template from 22P4F11 cDNA. The PCR product is subcloned into pSRαMSVtkneo via the EcoR1 (blunt-ended) and Xba 1 restriction sites on the vector and transformed into DH5α competent cells. Colonies are picked to screen for clones with unique internal restriction sites on the cDNA. The positive clone is confirmed by sequencing of the cDNA insert. Retroviruses are used for infection and generation of various cell lines using, for example, 3T3CL7, PC3, and LnCap cells.

Example 6

Production of Recombinant 22P4F11 in a Baculovirus System

To generate a recombinant 22P4F11 protein in a baculovirus expression system, the 22P4F11 cDNA is cloned into the baculovirus transfer vector pBlueBac 4.5 (Invitrogen) which provides a His-tag at the N-terminus Specifically, pBlueBac-22P4F11 is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 22P4F11 protein is then generated by infection of HighFive insect cells (InVitrogen) with the purified baculovirus. Recombinant 22P4F11 protein may be detected using anti-22P4F11 antibody. 22P4F11 protein may be purified and used in various cell based assays or as immunogen to generate polyclonal and monoclonal antibodies specific for 22P4F11.

Example 7

Identification of Potential Signal Transduction Pathways

To determine whether 22P4F11 directly or indirectly activates known signal transduction pathways in cells, luciferase (luc) based transcriptional reporter assays are carried out in cells expressing 22P4F11. These transcriptional reporters contain consensus binding sites for known transcription factors which lie downstream of well characterized signal transduction pathways. The reporters and examples of there associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress 2P4F11-mediated effects may be assayed in cells showing mRNA expression. Luciferase reporter plasmids may be introduced by lipid mediated transfection (TFX-50, Promega). Luciferase activity, an indicator of relative transcriptional activity, is measured by incubation of cells extracts with luciferin substrate and luminescence of the reaction is monitored in a luminometer.

Example 8

Generation of 22P4F11 Monoclonal Antibodies

In order to generate 22P4F11 monoclonal antibodies, a glutathione-S-transferase (GST) fusion protein encompassing a 22P4F11 protein is synthesized and used as immunogen. Balb C mice are initially immunized intraperitoneally with 200 µg of the GST-22P4F11 fusion protein mixed in complete Freund's adjuvant. Mice are subsequently immunized every 2 weeks with 75 µg of GST-22P4F11 protein mixed in Freund's incomplete adjuvant for a total of 3 immunizations. Reactivity of serum from immunized mice to full length 22P4F11 protein is conveniently monitored by ELISA using a partially purified preparation of HIS-tagged 22P4F11 protein expressed from 293T cells. Mice showing the strongest reactivity are rested for 3 weeks and given a final injection of fusion protein in PBS and then sacrificed 4 days later. The spleens of the sacrificed mice are then harvested and fused to SPO/2 myeloma cells using standard procedures (Harlow and Lane, 1988). Supernatants from growth wells following HAT selection are screened by ELISA and Western blot to identify 22P4F11 specific antibody producing clones.

The binding affinity of a 22P4F11 monoclonal antibody may be determined using standard technology. Affinity measurements quantify the strength of antibody to epitope binding and may be used to help define which 22P4F11 monoclonal antibodies are preferred for diagnostic or therapeutic use. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 9

In Vitro Assays of 22P4F11 Function

The expression of 22P4F11 in prostate cancer suggests a possible functional role in tumor progression. 22P4F11 function can be assessed in mammalian cells using in vitro approaches. For mammalian expression, 22P4F11 can be cloned into a number of appropriate vectors, including pcDNA 3.1 myc-His-tag (Example 6) and the retroviral vector pSRαtkneo (Muller et al., 1991, MCB 11:1785). Using such expression vectors, 22P4F11 can be expressed in several cell lines, including PC-3, NIH 3T3, LNCaP and 293T. Expression of 22P4F11 can be monitored using anti-22P4F11 antibodies.

Mammalian cell lines expressing 22P4F11 can be tested in several in vitro and in vivo assays, including cell proliferation in tissue culture, activation of apoptotic signals, tumor formation in SCID mice, and in vitro invasion using a membrane invasion culture system (MICS) (Welch et al., Int. J. Cancer 43: 449-457). 22P4F11 cell phenotype is compared to the phenotype of cells that lack expression of 22P4F11.

Cell lines expressing 22P4F11 can also be assayed for alteration of invasive and migratory properties by measuring passage of cells through a matrigel coated porous membrane chamber (Becton Dickinson). Passage of cells through the membrane to the opposite side is monitored using a fluorescent assay (Becton Dickinson Technical Bulletin #428) using calcein-Am (Molecular Probes) loaded indicator cells. Cell lines analyzed include parental and 22P4F11 overexpressing PC3, 3T3 and LNCaP cells. To assay whether 22P4F11 has chemoattractant properties, parental indicator cells are monitored for passage through the porous membrane toward a gradient of 22P4F11 conditioned media compared to control media. This assay may also be used to qualify and quantify specific neutralization of the 22P4F11 induced effect by candidate cancer therapeutic compositions.

Example 10

In Vivo Assay for 22P4F11 Tumor Growth Promotion

The effect of the 22P4F11 protein on tumor cell growth may be evaluated in vivo by gene overexpression in tumor-bearing mice. For example, SCID mice can be injected SQ on each flank with 1×106 of either PC3, TSUPR1, or DU145 cells containing tkNeo empty vector or 22P4F11. At least two strategies may be used: (1) Constitutive 22P4F11 expression under regulation of an LTR promoter, and (2) Regulated expression under control of an inducible vector system, such as ecdysone, tet, etc. Tumor volume is then monitored at the appearance of palpable tumors and followed over time to determine if 22P4F11 expressing cells grow at a faster rate. Additionally, mice may be implanted with 1×105 of the same cells orthotopically to determine if 22P4F11 has an effect on local growth in the prostate or on the ability of the cells to metastasize, specifically to lungs, lymph nodes, and bone marrow.

The assay is also useful to determine the 22P4F11 inhibitory effect of candidate therapeutic compositions, such as for example, 22P4F11 intrabodies, 22P4F11 antisense molecules and ribozymes.

The invention claimed is:

1. An isolated antibody or antigen binding fragment thereof that specifically binds to a polypeptide comprising the amino acid sequence SEQ ID NO: 2.

2. The antibody or fragment of claim 1, wherein the polypeptide is encoded by a polynucleotide having the sequence of SEQ ID NO: 1.

3. The antibody or fragment of claim 1, wherein the polypeptide is encoded by a polynucleotide having the sequence of SEQ ID NO: 1, from nucleotide residue number 306 through nucleotide residue number 1466.

4. The antibody or fragment of claim 1, wherein the polypeptide is encoded by a polynucleotide encoded by the cDNA contained in the plasmid deposited with American Type Culture Collection as Accession Nos. 98985.

5. An isolated antibody or fragment thereof that specifically binds to a polypeptide with the amino acid sequence shown in SEQ ID NO: 2.

6. The antibody or fragment of claim 1, wherein the antibody is a polyclonal antibody.

7. The antibody or fragment of claim 1, wherein the antibody is a human antibody, a humanized antibody, or a chimeric antibody.

8. The antibody or fragment of claim 1, wherein the antibody is a monoclonal antibody.

9. The antibody or fragment of claim 8, wherein the monoclonal antibody is recombinantly produced.

10. The antibody or fragment of claim 9, wherein the recombinant protein comprises the antigen binding region.

11. The antibody or fragment of claim 8, wherein the fragment thereof is selected from the group consisting of Fab, F(ab')2, Fv and sFv fragment.

12. A hybridoma that produces the monoclonal antibody of claim 8.

13. A pharmaceutical composition that comprises the antibody or fragment thereof of claim 1 and a physiologically acceptable carrier.

14. The antibody or fragment of claim 1, further labeled with a detectable marker.

15. The antibody or fragment of claim 14, wherein the detectable marker is selected from the group consisting of a radioisotope, a fluorescent compound, a bioluminescent compound, a chemiluminescent compound, a metal chelator and an enzyme.

16. A single chain antibody that comprises the variable domains of the heavy and light chains of a monoclonal antibody of claim 8.

* * * * *

SEQUENCE LISTING

<160> NUMBER OF SEQ ID NOS: 16

<210> SEQ ID NO 1
<211> LENGTH: 2251
<212> TYPE: DNA
<213> ORGANISM: Homo sapiens

<400> SEQUENCE: 1

```
aaaacaggct ggtaccggtc cggaattccc gggatatcgt cgacccacgc gtccggagag      60
aaactataat gataatttct accaggagat tttcttaatt aactctgtga aagattagct     120
tcaatgtctt aatttcacag atgatacaaa gaatggttaa atgagtgttt caaaaactct     180
gatagaaaca agaatttatt ttatgattaa atttcagtcc attatgattt tcctttctca     240
cataattact tttttctttt tagacttata agctagcaat tacagattta actacagcta     300
tcagcatgga caaaaatagt tatacagcat tttataacag agcattatgt tacaccaaga     360
taagggaact tcaaatggca ttaacagatt atggaattgt gctgcttctt gatgctacag     420
aaactgtaaa actaaatacc ttccttaatc gtggactcat ctacgtagaa ctaggccagt     480
atggctttgc actagaggat tttaaacaag ctgcactgat aagccggact aacgggagcc     540
tttgtcacgc cactgccatg tgccatcaca gaattaatga gtttgaagaa gctgtcaatt     600
tctttacttg ggctcttaaa attaacccat gttttctgga tgcttatgtt ggacggggaa     660
attcttacat ggaatacggt catgatgaag ccaccaagca agcacagaaa gactttctga     720
aagcactgca tattaatcca gcatacataa aagccagaat tagtttttggc tataatttgc     780 aggcccaagg aaaattccag aaagcttgga accactttac cattgccata gatactgatc     840
caaagaacta cctagcctat gaaggaagag ctgtggtctg tcttcagatg ggtaataatt     900
ttgctgcaat gcaggatatt aatgctgcca tgaagatcag tactacagca gaattcttaa     960
```

-continued

```
caaatcgtgg ggtgattcat gagtttatgg gccacaaaca gaatgcaatg aaagactacc    1020
aagatgcaat tactctaaac cccaagtact cgctggctta ctttaatgca ggaaatatct    1080
actttcacca caggcagttt tcccaggcca gtgactactc tcaaaagct ttaaaatttg     1140 atccagaaaa tgaatatgtt ctcatgaatc gagctattac aaatacaata ttaaagaaat    1200
atgaagaagc aaaagaagat tttgcaaatg taattgaaag ctgtcccttt tgggctgcag    1260
tatattttaa tagagcacat ttctactact gcttaaagca atatgaacta gctgaggaag    1320
accttaataa agccctgtct ttgaagccta atgatgctct agtatataat tttagagcaa    1380
aagttcgtgg taaaataggt ctgattgagg aagctatggc tgactataac caagcacttg    1440
atcttgaaga ctatgcctca gttatatgat tacatagact gtggttgcta tagtagttta    1500
cacagctgtt ctctctgaaa cggaaacata tttgttgtct aaaaggttct accatttca    1560 ttattgtatt cgttatgctt agtcttccat ataaccttct atgcatttta ataaaatgtt    1620
tgttatacat taattataaa acatatatca tttgctgcat atttggaata ccttgagaac    1680 tgaattttc caaggttgca gaatctcaag gaaaatgttt cttaaggaat taaataggaa     1740
tgtctcttaa catttaaaat attttcttta attcttttg aaataatact atacattgta     1800 gaaaagtgt cattgacctt tcatcagtc cttgctgaca atgtattaaa cagtatacag      1860
attaaaaata aacaaaccga tgactataaa aaactgaact caagtacaac ccttctcttt    1920
tcctttaaac aatatgtata ctggtcaata ttcttcctga tacctatatt cttccaacag    1980
acaaacgtgt ttctctttta catgtggcct gccttctagg acagtaccta taagattttt    2040
ggacatcatg tttccttgag atagttccct ctgcctcttt aatgcagcta tcataaatac    2100
atgtaaaatt tgtatatatt tataattcat gcattgcagg agttgatgag tgaaaataaa    2160
acaactaaaa attaaaaaaa aaaaaaaaa agggcggccg ctctagagta tccctcgagg    2220
ggcccaagct tacgcgtacc cagctttctt g                                   2251
```

<210> SEQ ID NO 2
<211> LENGTH: 387
<212> TYPE: PRT
<213> ORGANISM: Homo sapiens

<400> SEQUENCE: 2

```
Met Asp Lys Asn Ser Tyr Thr Ala Phe Tyr Asn Arg Ala Leu Cys Tyr
  1               5                  10                  15

Thr Lys Ile Arg Glu Leu Gln Met Ala Leu Thr Asp Tyr Gly Ile Val
             20                  25                  30

Leu Leu Leu Asp Ala Thr Glu Thr Val Lys Leu Asn Thr Phe Leu Asn
         35                  40                  45

Arg Gly Leu Ile Tyr Val Glu Leu Gly Gln Tyr Gly Phe Ala Leu Glu
     50                  55                  60

Asp Phe Lys Gln Ala Ala Leu Ile Ser Arg Thr Asn Gly Ser Leu Cys
 65                  70                  75                  80

His Ala Thr Ala Met Cys His His Arg Ile Asn Glu Phe Glu Glu Ala
                 85                  90                  95

Val Asn Phe Phe Thr Trp Ala Leu Lys Ile Asn Pro Cys Phe Leu Asp
            100                 105                 110

Ala Tyr Val Gly Arg Gly Asn Ser Tyr Met Glu Tyr Gly His Asp Glu
        115                 120                 125

Ala Thr Lys Gln Ala Gln Lys Asp Phe Leu Lys Ala Leu His Ile Asn
    130                 135                 140
```

Pro Ala Tyr Ile Lys Ala Arg Ile Ser Phe Gly Tyr Asn Leu Gln Ala
145                 150                 155                 160

Gln Gly Lys Phe Gln Lys Ala Trp Asn His Phe Thr Ile Ala Ile Asp
            165                 170                 175

Thr Asp Pro Lys Asn Tyr Leu Ala Tyr Glu Gly Arg Ala Val Val Cys
            180                 185                 190

Leu Gln Met Gly Asn Asn Phe Ala Ala Met Gln Asp Ile Asn Ala Ala
            195                 200                 205

Met Lys Ile Ser Thr Thr Ala Glu Phe Leu Thr Asn Arg Gly Val Ile
210                 215                 220

His Glu Phe Met Gly His Lys Gln Asn Ala Met Lys Asp Tyr Gln Asp
225                 230                 235                 240

Ala Ile Thr Leu Asn Pro Lys Tyr Ser Leu Ala Tyr Phe Asn Ala Gly
            245                 250                 255

Asn Ile Tyr Phe His His Arg Gln Phe Ser Gln Ala Ser Asp Tyr Phe
            260                 265                 270

Ser Lys Ala Leu Lys Phe Asp Pro Glu Asn Glu Tyr Val Leu Met Asn
            275                 280                 285

Arg Ala Ile Thr Asn Thr Ile Leu Lys Lys Tyr Glu Glu Ala Lys Glu
            290                 295                 300

Asp Phe Ala Asn Val Ile Glu Ser Cys Pro Phe Trp Ala Ala Val Tyr
305                 310                 315                 320

Phe Asn Arg Ala His Phe Tyr Tyr Cys Leu Lys Gln Tyr Glu Leu Ala
            325                 330                 335

Glu Glu Asp Leu Asn Lys Ala Leu Ser Leu Lys Pro Asn Asp Ala Leu
            340                 345                 350

Val Tyr Asn Phe Arg Ala Lys Val Arg Gly Lys Ile Gly Leu Ile Glu
            355                 360                 365

Glu Ala Met Ala Asp Tyr Asn Gln Ala Leu Asp Leu Glu Asp Tyr Ala
            370                 375                 380

Ser Val Ile
385

<210> SEQ ID NO 3
<211> LENGTH: 207
<212> TYPE: DNA
<213> ORGANISM: Homo sapiens

<400> SEQUENCE: 3
atcagtacta cagcagaatt cttaacaaat cgtggggtga ttcatgagtt tatgggccac      60
aaacagaatg caatgaaaga ctaccaagat gcaattactc taaaccccaa gtactcgctg     120
gcttacttta atgcaggaaa tatctacttt caccacaggc agttttccca ggccagtgac     180
tacttctcaa aagctttaaa atttgat                                         207

<210> SEQ ID NO 4
<211> LENGTH: 69
<212> TYPE: PRT
<213> ORGANISM: Homo sapiens

<400> SEQUENCE: 4

Ile Ser Thr Thr Ala Glu Phe Leu Thr Asn Arg Gly Val Ile His Glu
1               5                   10                  15

Phe Met Gly His Lys Gln Asn Ala Met Lys Asp Tyr Gln Asp Ala Ile
            20                  25                  30

Thr Leu Asn Pro Lys Tyr Ser Leu Ala Tyr Phe Asn Ala Gly Asn Ile
    35                  40                  45

Tyr Phe His His Arg Gln Phe Ser Gln Ala Ser Asp Tyr Phe Ser Lys
    50                  55                  60

Ala Leu Lys Phe Asp
 65

<210> SEQ ID NO 5
<211> LENGTH: 14
<212> TYPE: DNA
<213> ORGANISM: Artificial Sequence
<220> FEATURE:
<223> OTHER INFORMATION: cDNA synthesis primer

<400> SEQUENCE: 5
ttttgatcaa gctt                                                          14

<210> SEQ ID NO 6
<211> LENGTH: 42
<212> TYPE: DNA
<213> ORGANISM: Artificial Sequence
<220> FEATURE:
<223> OTHER INFORMATION: DNA Adaptor 1

<400> SEQUENCE: 6
ctaatacgac tcactatagg gctcgagcgg ccgcccgggc ag                            42

<210> SEQ ID NO 7
<211> LENGTH: 40
<212> TYPE: DNA
<213> ORGANISM: Artificial Sequence
<220> FEATURE:
<223> OTHER INFORMATION: DNA Adaptor 2

<400> SEQUENCE: 7
gtaatacgac tcactatagg gcagcgtggt cgcggccgag                               40

<210> SEQ ID NO 8
<211> LENGTH: 22
<212> TYPE: DNA
<213> ORGANISM: Artificial Sequence
<220> FEATURE:
<223> OTHER INFORMATION: PCR primer 1

<400> SEQUENCE: 8
ctaatacgac tcactatagg gc                                                 22

<210> SEQ ID NO 9
<211> LENGTH: 22
<212> TYPE: DNA
<213> ORGANISM: Artificial Sequence
<220> FEATURE:
<223> OTHER INFORMATION: Nested primer(NP)1

<400> SEQUENCE: 9
tcgagcggcc gcccgggcag ga                                                 22

<210> SEQ ID NO 10
<211> LENGTH: 20
<212> TYPE: DNA
<213> ORGANISM: Artificial Sequence
<220> FEATURE:
<223> OTHER INFORMATION: Nested primer(NP)2

<400> SEQUENCE: 10

-continued agcgtggtcg cggccgagga                                                20

<210> SEQ ID NO 11
<211> LENGTH: 24
<212> TYPE: DNA
<213> ORGANISM: Artificial Sequence
<220> FEATURE:
<223> OTHER INFORMATION: RT-PCR primer

<400> SEQUENCE: 11
gccacaaaca gaatgcaatg aaag                                           24

<210> SEQ ID NO 12
<211> LENGTH: 23
<212> TYPE: DNA
<213> ORGANISM: Artificial Sequence
<220> FEATURE:
<223> OTHER INFORMATION: RT-PCR primer

<400> SEQUENCE: 12
aaactgcctg tggtgaaagt aga                                            23

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
atatcgccgc gctcgtcgtc gacaa                                          25

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14
agccacacgc agctcattgt agaagg                                         26

<210> SEQ ID NO 15
<211> LENGTH: 12
<212> TYPE: DNA
<213> ORGANISM: Artificial Sequence
<220> FEATURE:
<223> OTHER INFORMATION: Adaptor 1 (additional chain)

<400> SEQUENCE: 15
gatcctgccc gg                                                        12

<210> SEQ ID NO 16
<211> LENGTH: 10
<212> TYPE: DNA
<213> ORGANISM: Artificial Sequence
<220> FEATURE:
<223> OTHER INFORMATION: Adaptor 2 (additional chain)

<400> SEQUENCE: 16
gatcctcggc                                                           10